US010512691B2

(12) United States Patent
Kalifa et al.

(10) Patent No.: US 10,512,691 B2
(45) Date of Patent: Dec. 24, 2019

(54) SYSTEMS AND METHODS FOR TARGETED IMAGING AND ABLATION OF CARDIAC CELLS

(71) Applicants: THE REGENTS OF THE UNIVERSITY OF MICHIGAN, Ann Arbor, MI (US); Jerome Kalifa, Oak Park, MI (US); Raoul Kopelman, Ann Arbor, MI (US); Uma Mahesh R. Avula, Ypsilanti, MI (US); Gwangseong Kim, Ann Arbor, MI (US); Yong-Eun Koo Lee, Seoul (KR); Hyung Ki Yoon, Ann Arbor, MI (US)

(72) Inventors: Jerome Kalifa, Oak Park, MI (US); Raoul Kopelman, Ann Arbor, MI (US); Uma Mahesh R. Avula, Ypsilanti, MI (US); Gwangseong Kim, Ann Arbor, MI (US); Yong-Eun Koo Lee, Seoul (KR); Hyung Ki Yoon, Ann Arbor, MI (US)

(73) Assignee: THE REGENTS OF THE UNIVERSITY OF MICHIGAN, Ann Arbor, MI (US)

(\*) Notice: Subject to any disclaimer, the term of this patent is extended or adjusted under 35 U.S.C. 154(b) by 341 days.

(21) Appl. No.: 14/396,533

(22) PCT Filed: Apr. 23, 2013

(86) PCT No.: PCT/US2013/037807
§ 371 (c)(1),
(2) Date: Oct. 23, 2014

(87) PCT Pub. No.: WO2013/163187
PCT Pub. Date: Oct. 31, 2013

(65) Prior Publication Data
US 2015/0328315 A1 Nov. 19, 2015

Related U.S. Application Data

(60) Provisional application No. 61/637,241, filed on Apr. 23, 2012.

(51) Int. Cl.
| A61K 51/00 | (2006.01) |
| A61K 41/00 | (2006.01) |
| A61K 31/5415 | (2006.01) |
| A61K 31/704 | (2006.01) |
| A61K 33/24 | (2019.01) |
| A61K 38/10 | (2006.01) |
| A61K 38/18 | (2006.01) |
| A61K 38/20 | (2006.01) |
| A61K 38/21 | (2006.01) |
| A61K 9/51 | (2006.01) |

(52) U.S. Cl.
CPC ........ *A61K 41/0057* (2013.01); *A61K 9/5138* (2013.01); *A61K 31/5415* (2013.01); *A61K 31/704* (2013.01); *A61K 33/24* (2013.01); *A61K 38/10* (2013.01); *A61K 38/18* (2013.01); *A61K 38/20* (2013.01); *A61K 38/21* (2013.01)

(58) Field of Classification Search
CPC ........ A61K 38/00; A61K 38/10; A61K 38/18; A61K 38/20; A61K 38/21; A61K 9/00; A61K 9/5138; A61K 31/00; A61K 31/5415; A61K 31/704; A61K 41/00; A61K 41/0057; A61K 33/00; A61K 33/24
USPC .... 424/1.11, 1.65, 1.69, 9.1, 9.2, 9.6; 514/1, 514/1.11, 19.2, 19.3, 19.4, 19.5, 19.6, 514/21.5; 530/300, 327
See application file for complete search history.

(56) References Cited

U.S. PATENT DOCUMENTS

| 8,562,944 | B2 | 10/2013 | Pandey et al. | |
| 8,709,472 | B1* | 4/2014 | Murase | A61K 47/42 424/1.69 |
| 8,906,343 | B2 | 12/2014 | Pandey et al. | |
| 9,045,488 | B2 | 6/2015 | Pandey et al. | |
| 9,249,184 | B2* | 2/2016 | Robbins | C07K 7/06 |
| 2003/0082101 | A1 | 5/2003 | Taylor et al. | |
| 2006/0073100 | A1* | 4/2006 | Fischman | A61B 5/0071 424/9.6 |

(Continued)

OTHER PUBLICATIONS

Aiba et al., "The role of Purkinje and pre-Purkinje potentials in the reentrant circuit of verapamil-sensitive idiopathic LV tachycardia." Pacing Clin Electrophysiol. Mar. 2001; 24(3):333-44.

(Continued)

*Primary Examiner* — D. L. Jones
(74) *Attorney, Agent, or Firm* — Casimir Jones, S.C.; Tanya Arenson

(57) ABSTRACT

The present invention relates to nanoparticles. In particular, the present invention provides nanoparticles for clinical (e.g., targeted therapeutic), diagnostic (e.g., imaging), and research applications in the field of cardiology. For example, in some embodiments, the present invention provides a method of treating (e.g., ablating) cardiac tissue, comprising: a) contacting an animal with a nanoparticle comprising a matrix, a toxic (e.g., ablative) agent (e.g., sonosensitizer, chemotherapeutic agent (e.g., doxorubicin or cisplatin), or photosensitizer), and a cardiac targeting moiety; and b) administering an activator of the toxic agent (e.g., light, chemical (e.g., pharmaceutical agent) or ultrasound) to at least a portion of the cardiac tissue (e.g., heart) of the animal to activate the toxic agent.

10 Claims, 8 Drawing Sheets
Specification includes a Sequence Listing.

(56) References Cited

U.S. PATENT DOCUMENTS

2009/0191633 A1* 7/2009 Shogbon ............. C12N 5/0068
                                                            435/396
2009/0257950 A1  10/2009 Sliger et al.
2010/0310495 A1  12/2010 Schneider et al.

OTHER PUBLICATIONS

Avula et al., "Cell-specific nanoplatform-enabled photodynamic therapy for cardiac cells" Heart Rhythm 2011, San Francisco, CA.
Blaauw et al., "Cardioversion of persistent atrial fibrillation by a combination of atrial specific and non-specific class III drugs in the goat." Cardiovasc Res. Jul. 1, 2007; 75(1):89-98.
Calkins et al., ""HRS/EHRA/ECAS Expert Consensus Statement onCatheter and Surgical Ablation of Atrial Fibrillation: Recommendations for Personnel, Policy, Procedures andFollow-Up"" Europace. Jun. 2007; 9(6):335-79.
Cappato et al., "Worldwide survey on the methods, efficacy, and safety of catheter ablation for human atrial fibrillation." Circulation. Mar. 8, 2005; 111(9):1100-5.
Chen et al., "Vascular and cellular targeting for photodynamic therapy." Crit Rev Eukaryot Gene Expr. 2006; 16 (4):279-305.
Cheng et al., "Highly efficient drug delivery with gold nanoparticle vectors for in vivo photodynamic therapy of cancer." J Am Chem Soc. Aug. 13, 2008; 130(32):10643-7.
Couleaud et al., "Silica-based nanoparticles for photodynamic therapy applications." Nanoscale. Jul. 2010; 2 (7):1083-95.
Daubresse et al., "Synthesis and inverse emulsion polymerization of aminated acrylamidodextran." J Pharm Pharmacol. Dec. 1993; 45(12):1018-23.
D'Hallewin et al., "Bladder spectrophotometry after intravesical Epirubicine instillations: Evaluation of future possibilities of topical bladder sensitization for PDT" Lasers in Medical Science Mar. 1990, 5(1): 13-15.
Dolmans et al., "Photodynamic therapy for cancer." Nat Rev Cancer. May 2003; 3(5):380-7.
Hah et al., "Methylene blue-conjugated hydrogel nanoparticles and tumor-cell targeted photodynamic therapy." Macromol Biosci. Jan. 10, 2011; 11(1):90-9.
Hettiaratchy et al., "Burns after photodynamic therapy." BMJ. May 6, 2000; 320(7244):1245.
Ito et al., "The myocardial electrical blockade induced by photosensitization reaction." IEEE Trans Biomed Eng. Feb. 2010; 57(2):488-95.
Kohsaka et al., "Idiopathic ventricular fibrillation successfully terminated by radiofrequency ablation of the distal Purkinje fibers." Pacing Clin Electrophysiol. May 2007; 30(5):701-4.
Koo et al., "Brain cancer diagnosis and therapy with nanoplatforms." Adv Drug Deliv Rev. Dec. 1, 2006;58 (14):1556-77.
Morady et al., "Transvenous catheter ablation of a posteroseptal accessory pathway in a patient with the Wolff-Parkinson-White syndrome." N Engl J Med. Mar. 15, 1984; 310(11):705-7.
Naccarelli et al., "A review of clinical trials assessing the efficacy and safety of newer antiarrhythmic drugs in atrial fibrillation." J Interv Card Electrophysiol. Oct. 2003; 9(2):215-22.
Nogami et al., "Demonstration of diastolic and presystolic Purkinje potentials as critical potentials in a macroreentry circuit of verapamil-sensitive idiopathic left ventricular tachycardia." J Am Coll Cardiol. Sep. 2000; 36(3):811-23.

Noguchi et al., "Synthesis of monomeric and polymeric conjugates carrying a thrombin inhibitor through an ester bond." J Biomed Mater Res. Mar. 15, 1998; 39(4):621-9.
Oral et al., ""Catheter Ablation for Paroxysmal Atrial Fibrillation Segmental Pulmonary Vein Ostial Ablation Versus Left Atrial Ablation"" Circulation. Nov. 11, 2003;108(19):2355-60.
Orringer et al., "The brain tumor window model: a combined cranial window and implanted glioma model for evaluating intraoperative contrast agents." Neurosurgery. Apr. 2010; 66(4):736-43.
Pappone et al., "Atrio-esophageal fistula as a complication of percutaneous transcatheter ablation of atrial fibrillation." Circulation. Jun. 8, 2004; 109(22):2724-6.
Podrid, "Proarrhythmia, a serious complication of antiarrhythmic drugs." Curr Cardiol Rep. Nov. 1999; 1(4):289-96.
Robbins et al., "Pulmonary vein stenosis after catheter ablation of atrial fibrillation." Circulation. Oct. 27, 1998; 98 (17):1769-75.
Ross et al., "Photonic and magnetic nanoexplorers for biomedical use: from subcellular imaging to cancer diagnostics and therapy" Nanobiophotonics and Biomedical Applications, 76-83 (Jun. 1, 2004).
Sawhney et al., "Recovery of mitral isthmus conduction leads to the development of macro-reentrant tachycardia after left atrial linear ablation for atrial fibrillation." Circ Arrhythm Electrophysiol. Dec. 2011; 4(6):832-7.
Severino et al., "Influence of negatively charged interfaces on the ground and excited state properties of methylene blue." Photochem Photobiol. May 2003; 77(5):459-68.
Shah et al, "Acute pyloric spasm and gastric hypomotility: an extracardiac adverse effect of percutaneous radiofrequency ablation for atrial fibrillation." J Am Coll Cardiol. Jul. 19, 2005; 46(2):327-30.
Shum et al., "Phototriggering of liposomal drug delivery systems." Adv Drug Deliv Rev. Dec. 31, 2001; 53(3):273-84.
Sosa et al., "Left atrial-esophageal fistula complicating radiofrequency catheter ablation of atrial fibrillation." J Cardiovasc Electrophysiol. Mar. 2005; 16(3):249-50.
Suci et al., "Targeting and photodynamic killing of a microbial pathogen using protein cage architectures functionalized with a photosensitizer" Langmuir. Nov. 20, 2007; 23(24):12280-6.
Vasir et al., "Preparation of Biodegradable Nanoparticles and Their Use in Transfection" Cold Spring Harbor Protocols 2008.
Vos, "Atrial-specific drugs: the way to treat atrial fibrillation?" J Cardiovasc Electrophysiol. Dec. 2004; 15(12):1451-2.
Weerasooriya et al., "Catheter ablation for atrial fibrillation: are results maintained at 5 years of follow-up?" J Am Coll Cardiol. Jan. 11, 2011; 57(2):160-6.
Weerasooriya et al., "Catheter Ablation of Ventricular Fibrillation in Structurally Normal Hearts Targeting the RVOT and Purkinje Ectopy." Herz. Nov. 2003; 28(7):598-606.
Winer et al., "F3-targeted cisplatin-hydrogel nanoparticles as an effective therapeutic that targets both murine and human ovarian tumor endothelial cells in vivo." Cancer Res. Nov. 1, 2010; 70(21):8674-83.
Yang et al., "Increasing the efficiency of photodynamic therapy by improved light delivery and oxygen supply using an anticoagulant in a solid tumor model." Lasers Surg Med. Sep. 2010; 42(7):671-9.
Zahid et al., "Identification of a cardiac specific protein transduction domain by in vivo biopanning using a M13 phage peptide display library in mice." PLoS One. Aug. 17, 2010; 5(8):e12252.

* cited by examiner

A. Non-targeted PDT

B. CTP targeted PDT

A

B ered by reference in its entirety.

SEQUENCE LISTING

```
<160> NUMBER OF SEQ ID NOS: 1

<210> SEQ ID NO 1
<211> LENGTH: 12
<212> TYPE: PRT
<213> ORGANISM: Artificial Sequence
<220> FEATURE:
<223> OTHER INFORMATION: Synthetic

<400> SEQUENCE: 1

Ala Pro Trp His Leu Ser Ser Gln Tyr Ser Arg Thr
1               5                   10
```

SYSTEMS AND METHODS FOR TARGETED IMAGING AND ABLATION OF CARDIAC CELLS This application is a national phase application under 35 U.S.C. § 371 of PCT International Application No. PCT/US2013/037807, filed Oct. 23, 2013, which claims priority to U.S. Provisional Patent Application No. 61/637,241, filed Apr. 23, 2012, each of which are herein incorporated by reference in its entirety.

STATEMENT REGARDING FEDERALLY SPONSORED RESEARCH OR DEVELOPMENT

This invention was made with government support under grant HL111876 awarded by the National Institutes of Health. The government has certain rights in the invention.

FIELD OF THE INVENTION

The present invention relates to nanoparticles. In particular, the present invention provides nanoparticles for clinical (e.g., targeted therapeutic), diagnostic (e.g., imaging), and research applications in the field of cardiology.

BACKGROUND OF THE INVENTION

Atrial fibrillation (AF) is the leading cause of hospitalization due to cardial arrhythmia. Current treatments for AF include pharmacological treatments, and surgical treatments such as catheter ablation, with or without using implantable devices, and pace makers.

Over the last decades, various cardiac ablation technologies and procedures have been developed for patients with drug-resistant cardiac arrhythmias. It is now widely accepted that in selected patient populations, catheter ablation is an advantageous alternative to lifelong pharmacologic treatment (Oral et al. Circulation 2003; 108:2355-2360; Morady et al., New England Journal of Medicine 1984; 310:705-707; Calkins et al., Europace 2007; 9:335). Ablation consists of delivering physical energy locally to specific myocardial regions so as to interrupt the pathway of electrical circuits perpetuating the arrhythmia. Regardless of the energy employed, radiofrequency, ultrasound or other, ablation techniques are severely limited by the non-specific nature of the resultant cellular damage. As an example, bystander cells such as fibroblasts, adipocytes or neurons, experience similar damage to myocytes perpetuating the arrhythmia, resulting in post-ablation complications such as cardiac perforation, atrioesophageal fistula, pulmonary veins stenosis, bleeding, coronary spasm or stroke (Cappato et al., Circulation 2005 Mar. 8, 2005; 111:1100-1105; Pappone et al., Circulation 2004 Jun. 8, 2004; 109:2724-2726; Sosa et al., J Cardiovasc Electrophysiol 2005 March 2005; 16:249-250; Robbins et al., Circulation 1998; 98:1769-1775). Besides, this lack of cellular discrimination markedly increases the required energy amounts and prolongs procedure times, all of which reduces overall ablation efficacy. For instance, about 50% of patients undergoing catheter ablation for persistent atrial fibrillation (AF) will experience an arrhythmia recurrence which will require a redo procedure (Weerasooriya et al., Journal of the American College of Cardiology 2011; 57:160-166). Also, trans-mural lesions in specific regions of the heart, such as the mitral isthmus of the left atrium, are difficult to achieve with radio frequency technology, and incomplete lesions may set the stage for arrhythmia recurrence (Sawhney et al., Circulation: Arrhythmia and Electrophysiology 2011).

Improved methods of ablation to treat disorders such as AF are needed.

SUMMARY OF THE INVENTION

The present invention relates to nanoparticles. In particular, the present invention provides nanoparticles for clinical (e.g., targeted therapeutic), diagnostic (e.g., imaging), and research applications in the field of cardiology.

Embodiments of the present invention provide improved methods of treating cardiac arrhythmias (e.g., atrial fibrulation, premature atrial contractions, wandering atrial pacemaker, multifocal atrial tachycardia, atrial flutter, supraventricular tachycardia, tachycardia, junctional rhythm, junctional tachycardia, premature junctional contraction, premature ventricular contractions, accelerated idioventricular rhythm, monomorphic ventricular tachycardia, polymorphic ventricular tachycardia, ventricular fibrillation, heart blocks, long QT syndrome, Brugada syndrome, catecholaminergic polymorphic ventricular tachycardia, and arrhythmogenic right ventricular dysplasia and abnormal Purkinje potentioals leading to ventricular arrhythmias including electrical storms, using targeted (e.g., sonodynamic or photodynamic) therapy.

For example, in some embodiments, the present invention provides a method of treating (e.g., ablating) cardiac tissue, comprising: a) contacting an animal with a nanoparticle comprising a matrix, a toxic (e.g., ablative) agent (e.g., sonosensitizer, chemotherapeutic agent (e.g., doxorubicin or cisplatin), or photosensitizer), and a cardiac targeting moiety; and b) administering an activator of the toxic agent (e.g., light, chemical (e.g., pharmaceutical agent) or ultrasound) to at least a portion of the cardiac tissue (e.g., heart) of the animal to activate the toxic agent. In some embodiments, administering the activator kills (e.g., ablates) cardiac tissue only where activator is administered and only to targeted cells. In some embodiments, the activator is light or ultrasound. In some embodiments, light from a laser (e.g., administered via open heart surgery or via a catheter or other mechanism). In some embodiments, the activator is a pharmaceutical agent (e.g., administered orally or intravenously). In some embodiments, the cardiac targeting moiety is a cardiac targeting peptide (e.g., SEQ ID NO:1). In some embodiments, the photosensitizer is methylene blue, Photofrin, 2-devinyl-2-(1-hexyloxyethyl) pyropheophorbide (HPPH), chlorin e6 (Ce6), coomassie blue, or gold. In some embodiments, the contacting is via intravenous administration. In some embodiments, the cardiac targeting moiety specifically targets cardiac myocytes. In some embodiments, the nanoparticle is a PEG molecule (e.g., 8-arm PEG). In some embodiments, the nanoparticle is approximately 10 nm or less in size.

In some embodiments, the animal is a human. For example, in some embodiments, the animal exhibits signs or symptoms of atrial fibrillation and the ablating reduces or eliminates the signs or symptoms.

In some embodiments, the method further comprises the step of imaging the nanoparticles in the animal. In some embodiments, the imaging is performed after the administering of activator and optionally determines a treatment course of action (e.g., further administering of activator, location of treatment and/or nanoparticles). In some embodiments, the nanoparticles further comprise an imaging contrast agent (e.g., gold, iron oxide, iodine, etc.) or are designed to have imageable properties themselves. In some embodiments, the method further comprises the step of visualizing the imaging agent in the animal (e.g., via X-ray imaging, PET, photoacoustic imaging, ultrasound, computer tomography (CT) imaging, or magnetic resonance imaging (MRI)).

In further embodiments, the present invention provides compositions and kits comprising the aforementioned nanoparticles and any additional components necessary, sufficient or useful in cardiac ablation and imaging.

In yet other embodiments, the present invention provides the use of the aforementioned nanoparticles (e.g., in cardiac ablation or treatment of cardiac arrhythmias). In still further embodiments, the present invention provides systems comprising a) the aforementioned nanoparticles; and b) an instrument for delivery of activator (e.g., a laser or ultrasound instrument). In some embodiments, systems further comprise imaging components (e.g., to image nanoparticles in cardiac tissue) and computer software and computer processor for controlling the system. In some embodiments, the computer software and computer processor are configured to control the delivery of the activator, image the nanoparticle, and displaying an image of the nanoparticle.

Additional embodiments are described herein.

DEFINITIONS

Figure 1:
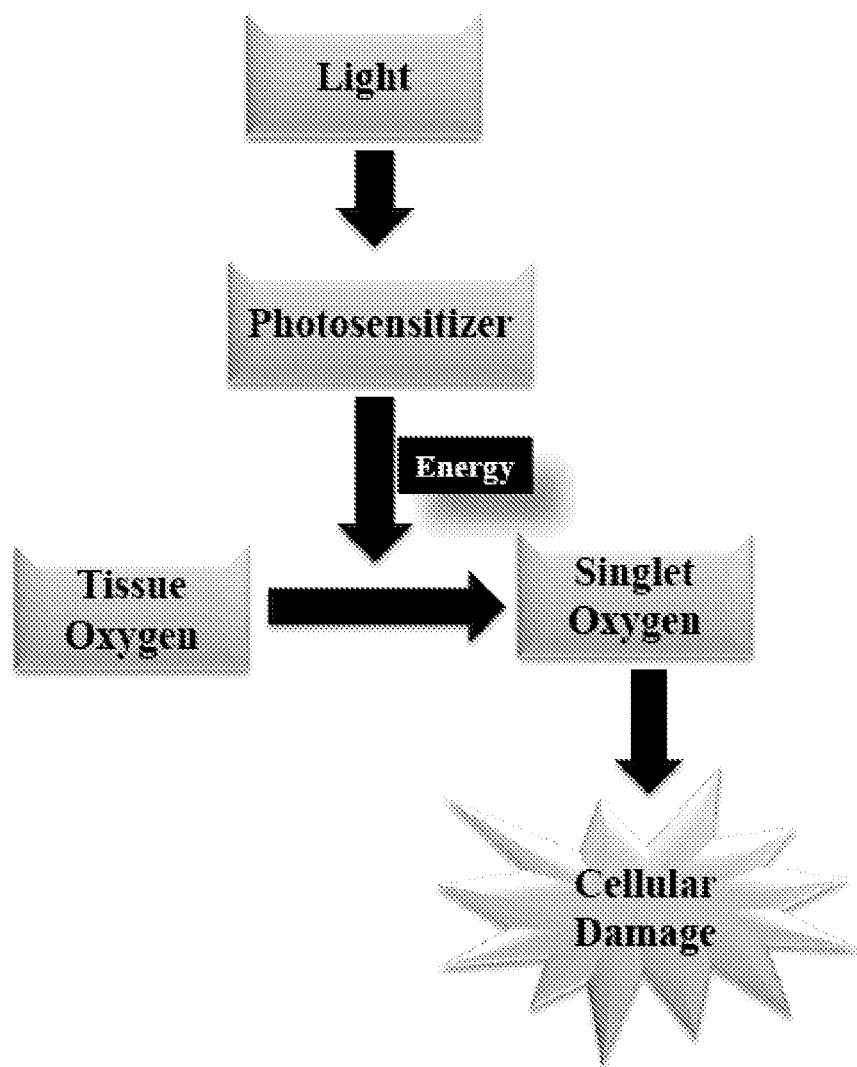
FIG. 1 shows a schematic of the principle of photodynamic therapy.

As used herein, the term "agent" refers to a composition that possesses a biologically relevant activity or property. Biologically relevant activities are activities associated with biological reactions or events that allow the detection, monitoring, or characterization of biological reactions or events. Biologically relevant activities include, but are not limited to, therapeutic activities (e.g., the ability to improve biological health or prevent the continued degeneration associated with an undesired biological condition), targeting activities (e.g., the ability to bind or associate with a biological molecule or complex), monitoring activities (e.g., the ability to monitor the progress of a biological event or to monitor changes in a biological composition), imaging activities (e.g., the ability to observe or otherwise detect biological compositions or reactions), and signature identifying activities (e.g., the ability to recognize certain cellular compositions or conditions and produce a detectable response indicative of the presence of the composition or condition). The agents of the present invention are not limited to these particular illustrative examples. Indeed any useful agent may be used, including agents that deliver or destroy biological materials, cosmetic agents, and the like.

As used herein, the term "purified" or "to purify" refers to the removal of contaminants from a sample. For example, antibodies are purified by removal of contaminating non-immunoglobulin proteins; they are also purified by the removal of immunoglobulin that does not bind the target protein. The removal of non-immunoglobulin proteins and/or the removal of immunoglobulins that do not bind the target protein results in an increase in the percent of target reactive immunoglobulins in the sample.

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

As used herein, the term "sample" is used in its broadest sense. In one sense, it is meant to include a specimen or culture obtained from any source, including biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. These examples are not to be construed as limiting the sample types applicable to the present invention.

DETAILED DESCRIPTION OF THE INVENTION

The present invention relates to nanoparticles. In particular, the present invention provides nanoparticles for clinical (e.g., targeted therapeutic), diagnostic (e.g., imaging), and research applications, for example, in the field of cardiac electrophysiology.

Embodiments of the present invention provide compositions, systems and methods for specifically targeting cardiac cells. In some embodiments, the present invention utilizes nanoparticles for targeting. The nanoparticles comprise: a) a targeting agent that targets the nanoparticles to a particular cardiac cell; b) a toxic agent that, when activated, destroys or kills the cells; and optionally c) an imaging agent.

Further embodiments of the present invention provide systems for delivery and activation of cardiac targeted nanoparticles. For example, in some embodiments, the systems include nanoparticles and an apparatus for activating and/or imaging the nanoparticle.

I. Nanoparticles

As described herein, embodiments of the present invention provide nanoparticles for cardiac targeted therapy and diagnostic applications. Exemplary nanoparticles are described herein.

A. Matrix

In some embodiments, nanoparticles are fabricated from a polymeric material (See e.g., Hah et al., Macromolecular bioscience 2011, herein incorporated by reference in its entirety). In some embodiments, the nanoparticles are biodegradable matrices.

The present invention is not limited to a particular matrix material. Indeed, a variety of matrix materials are contemplated. In some embodiments, a polymeric matrix (e.g., polyacrylamide or poly(vinyl chloride)) is utilized, while in other embodiments a glass matrix is utilized (e.g., sol-gel). In some embodiments of the present invention, the nanoparticles are finely ground or formed particles, with sizes ranging from 1 nm to 5 μm, preferably from about 5 to 400 nm. In some embodiments, nanoparticles are approximately 10 nm or less in size. The matrices can be hydrophobic (e.g., decyl-methacrylate), hydrophilic (e.g., polyacrylamide), or biodegradable (e.g., poly(lactic acid)).

In some embodiments, nanoparticles are fabricated from polyacrylamide. In some embodiments, about 27% acrylamide and about 3% N,N-methylene-bis(acrylamide) are combined in a buffer (e.g., 0.1M phosphate buffer, pH 6.5). About one ml of this solution is then added to a solution containing about 20 ml hexane, 1.8 mM sodium dioctyl sulfosuccinate, and about 4.24 mM Brij 30 (i.e., 4 lauryl ether). The solution is then stirred under nitrogen for 20 minutes while cooling in an ice bath. The polymerization is initiated with about 24 μl of a 10% ammonium persulfate solution and about 12 μl N'N'N',N'-tetraethyldiethylenetriamine (TEMED). The solution is then stirred at room temperature for about 2 hours. Hexane is removed by rotary evaporation, and the probes are rinsed free of surfactant with ethanol. This procedure yields particles of about 20 to 200 nm (Hah et al., *Macromolecular Bio Science* 11, p. 90-99, (2011)).

In other embodiments, nanoparticles are fabricated from poly(vinyl chloride). In some preferred embodiments, the poly(vinyl chloride) (e.g., about 33 wt %) is combined with a plasticizer (e.g., about 66 wt %) and dissolved in a solvent (e.g., about 200 mg of poly(vinyl chloride)/plasticizer mixture is added to 5 ml freshly distilled tetrahydrofuran (THF)). The solution is then coated onto polystyrene spheres of the desired size (e.g., about 10-1000 nm), and the coated spheres ground in liquid nitrogen.

In still other embodiments, the nanoparticles are fabricated from decy-methacrylate. In some embodiments, a polymerization solution is made by combining about 55 mg of decyl-methacrylate and about 75 mg of hexanediol dimethacrylate. The solution is then washed three times with 5% sodium hydroxide solution and three times with water. About 100 mg of dioctyl sebacate (DOS), 5 mg of benzophenone, and 2.5 mg of benzoyl peroxide are added to the washed monomer. This solution is then added to 1 ml of water and sonicated for 1 hour until uniform. The spheres are then purged with nitrogen for 20 min, and polymerized with a UV lamp for 15 min.

In still other embodiments, the nanoparticles are fabricated using a sol-gel procedure. In some embodiments, a polymerization solution is prepared comprising about 1.5 g sodium bis(2-ethylhexyl)sulfosuccinate (AOT), about 3 g Brij 30, about 9 ml hexane, about 4.5 ml tetraethylorthosilicate (TEOS), and about 250 ml $NH_3H_2O$. The solution is allowed to react for 18 hrs, with stirring, at room temperature.

In some embodiments, nanoparticles are fabricated from polyethylene glycol (PEG). In some embodiments, the method of generating PEG nanoparticles described in Example 3 is utilized.

In some embodiments, a co-polymer with functionalized groups or otherwise reactive groups (e.g., amine groups) is included during the fabrication of the nanoparticle. The co-polymer allows the convenient attachment of molecular recognition elements and other compounds (e.g., cloaking materials, biotin) to the particles. Useful co-polymers include, but are not limited to, (N-(3-Aminopropyl)methacrylamide hydrochloride) (APMA), acryloamidodextran, aminomethylstyrene, 2-hydroxyethyl acrylate, 2-hydroxymethacrylate, 4-hydroxybutyl acrylate (See e.g., Daubresse et al., J. Pharm. Pharmacol. 45(12):1018-23 [1993]; Noguchi et al., J. Biomed. Mat. Res. 39(4):621-9 [1998]).

B. Targeting Moieties

In some embodiments, nanoparticles comprise cardiac targeting moieties. In some embodiments, targeting moieties target myocytes. In some embodiments, the cardiac targeting moiety is cardiac targeting peptide (CTP) (Zahid et al., PloS one 2010; 5:e12252, herein incorporated by reference in its entirety). This peptide has the sequence APWHLSSQYSRT (SEQ ID NO:1). In some embodiments, variants (e.g., sequence variants) of cardiac targeting peptide that retain the ability to specifically bind to myocytes are utilized. Experiments conducted during the course of development of embodiments of the present invention demonstrated that 15 minutes post-peripheral intravenous injection in mice, CTP can efficiently and specifically transduce cardiac tissue. No other organ showed uptake except kidney glomeruli, limited to the cortex, and rare lung capillaries, to a much lesser extent than heart tissue. Thus, CTP is specific to the heart and cell type specific to myocytes. CTP also works in rat, and sheep and human (Zahid, et. al, supra).

In some embodiments, targeting moieties target additional cardiac cells (e.g., fibroblasts, Purkinje cells or cardiac nerve terminals).

The present invention is not limited to a particular targeting moiety. Any targeting moiety that specifically targets cardiac tissue (e.g., myocytes) is specifically contemplated for use in embodiments of the present invention. Examples include, but are not limited to, peptides, lipids, carbohydrates, nucleic acids and their derivatives (PNAs, LNAs etc.).

In some embodiments of the present invention, the targeting moiety is an antigen binding protein or antibody. Antibodies can be generated to allow for the targeting of antigens or immunogens (e.g., myocyte specific targets).

Such antibodies include, but are not limited to polyclonal, monoclonal, chimeric, single chain, Fab fragments, and a Fab expression library.

Various procedures known in the art are used for the production of polyclonal antibodies. For the production of antibody, various host animals can be immunized by injection with the peptide corresponding to the desired epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). Various adjuvants are used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette Guerin) and *Corynebacterium parvum*.

For preparation of monoclonal antibodies, any technique that provides for the production of antibody molecules by continuous cell lines in culture may be used (See, e.g., Harlow and Lane, Antibodies: A Laboratory Manual, Cold Spring Harbor Laboratory Press, Cold Spring Harbor, N.Y.). These include, but are not limited to, the hybridoma technique originally developed by Köhler and Milstein (Köhler and Milstein, Nature 256:495 497 [1975]), as well as the trioma technique, the human B cell hybridoma technique (See e.g., Kozbor et al. Immunol. Today 4:72 [1983]), and the EBV hybridoma technique to produce human monoclonal antibodies (Cole et al., in Monoclonal Antibodies and Cancer Therapy, Alan R. Liss, Inc., pp. 77 96 [1985]).

In an additional embodiment of the invention, monoclonal antibodies can be produced in germ free animals utilizing recent technology (See e.g., PCT/US90/02545). According to the invention, human antibodies may be used and can be obtained by using human hybridomas (Cote et al., Proc. Natl. Acad. Sci. U.S.A. 80:2026 2030 [1983]) or by transforming human B cells with EBV virus in vitro (Cole et al., in Monoclonal Antibodies and Cancer Therapy, Alan R. Liss, pp. 77 96 [1985]).

According to the invention, techniques described for the production of single chain antibodies (U.S. Pat. No. 4,946,778; herein incorporated by reference) can be adapted to produce specific single chain antibodies. An additional embodiment of the invention utilizes the techniques described for the construction of Fab expression libraries (Huse et al., Science 246:1275 1281 [1989]) to allow rapid and easy identification of monoclonal Fab fragments with the desired specificity.

Antibody fragments that contain the idiotype (antigen binding region) of the antibody molecule can be generated by known techniques. For example, such fragments include but are not limited to: the F(ab')2 fragment that can be produced by pepsin digestion of the antibody molecule; the Fab' fragments that can be generated by reducing the disulfide bridges of the F(ab')2 fragment, and the Fab fragments that can be generated by treating the antibody molecule with papain and a reducing agent.

In the production of antibodies, screening for the desired antibody can be accomplished by techniques known in the art (e.g., radioimmunoassay, ELISA (enzyme linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), Western Blots, precipitation reactions, agglutination assays (e.g., gel agglutination assays, hemagglutination assays, etc.), complement fixation assays, immunofluorescence assays, protein A assays, and immunoelectrophoresis assays, etc.).

In some embodiments of the present invention, the targeting moieties are nucleic acids (e.g., RNA or DNA). In some embodiments, the nucleic acid molecular recognition elements are designed to hybridize by base pairing to a particular nucleic acid (e.g., chromosomal DNA, mRNA, or ribosomal RNA).

Nucleic acids that bind ligands are preferably identified by the SELEX procedure (See e.g., U.S. Pat. Nos. 5,475,096; 5,270,163; and 5,475,096; and in PCT publications WO 97/38134, WO 98/33941, and WO 99/07724, all of which are herein incorporated by reference), although many methods are known in the art.

In some embodiments, nanoparticles are conjugated to PNAs. The present invention is not limited to a particular mechanism. Indeed, an understanding of the mechanism is not necessary to practice the present invention. Nonetheless, it is contemplated that replacing DNA with PNA or similar DNA analogs will lead to increased stability of the nucleic acid component of the nanoparticle and will, therefore, prolong targeting life of the nanoparticles and increase sequence selectivity. PNA/PNA binding affinity is extremely thermostable.

It is well established in the literature that PNAs have longer half-life in vivo and intracellularly compared to DNAs (McMahon et al., Antisense Nucleic Acid Drug Dev. 2002, 12, 65-70). However, the same body of research established that PNAs are not as soluble as DNAs and that some PNA sequences have proved difficult to synthesize in the past. The later issues have since been circumvented with the development of automated synthesis protocols (Mayfield et al., Anal. Biochem. 1999, 268, 401-404); while challenges of solubility and delivery of PNAs into cells were solved by new solubilization strategies For example, PNAs can be annealed to a negatively charged DNA oligonucleotide and complexed with cationic lipids for intracellular delivery (Braasch et al., Methods. 2001, 23, 97-107; Herbert et al., Proc. Natl. Acad. Sci. U.S.A. 1999, 96, 14276-14281). Alternative methods of intracellular delivery of PNAs include synthesis of a PNA with a nuclear localization signal (NLS) (Braun et al., J. Mol. Biol. 2002, 318, 237-243), electroporation (Karras et al., Biochemistry (Mosc). 2001, 40, 7853-7859; Shammas et al., Oncogene. 1999, 18, 6191-6200), and microinjection.

In some embodiments, targeting moieties are attached to the nanoparticle surface via covalent bonds. The targeting moieties can be attached to the nanoparticle by direct covalent bonding, or via functional ligands which also serve as an "electronic link" between these two nanocomposites components (as referenced in U.S. Pat. No. 6,677,606 B1, herein incorporated by reference in its entirety). Such ligands preferably have groups with varying donor acceptor character, selective binding of desired bio-active molecules (e.g., intracellular or extracellular targets), and components for the binding to the surface of the nanoparticles. Examples of the binding ligands include, but are not limited to, bidentate enediols, such as dopamine.

In some embodiments, nanoparticles comprise surface coatings (e.g., to improve uptake and retention, reduce toxicity, or improve targeting). For example, in some embodiments, nanocoparticles are coated with folic acid or glucose.

C. Toxic and Imaging Agents

In some embodiments, nanoparticles incorporate agents for therapy (e.g., photodynamic therapy) and/or imaging. In some embodiments, agents are embedded in the nanoparticles. In other embodiments, they are attached to the surface of particles.

In some embodiments, therapy is photodynamic therapy. For example, in some embodiments, agents for photodynamic therapy are photosensitizing agents. The present invention is not limited to a particular photosensitizing agent. In some embodiments, the agent is methylene blue (MB), chlorin e6 (Ce6), coomassie blue, gold, or other suitable photosensitizing agents. In some embodiments, the photosensitizing agent is also suitable for imaging (e.g., MB).

The present invention is not limited to photodynamic therapy. Additional therapeutic agents may be utilized in embodiment of the present invention. Examples include, but are not limited to, agents that induce apoptosis; sonosensitizers; polynucleotides (e.g., anti-sense, ribozymes, siRNA); polypeptides (e.g., enzymes and antibodies); agents that bind (e.g., oligomerize or complex) with a Bcl-2 family protein such as Bax; alkaloids; alkylating agents; antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-α) and interleukins (e.g., IL-2)); adoptive immunotherapy agents; hematopoietic growth factors; agents that induce cell differentiation (e.g., all-trans-retinoic acid); gene therapy reagents (e.g., antisense therapy reagents and nucleotides); angiogenesis inhibitors; proteosome inhibitors: NF-KB modulators; anti-CDK compounds; HDAC inhibitors; heavy metals (e.g., barium, gold, or platinum); chemotherapeutic agents (e.g., doxorubicin or cisplatin) and the like. Numerous other examples of toxic compounds are known to those skilled in the art.

In some embodiments, toxic agents are sonosensitizers. Examples of sonosensitizers include, but are not limited to, porphyrins (e.g., hematoporphyrin, diacetylhematoporphyn-mitomycin-C conjugate, photofrin II, mesoporphyrin, protoporphyrin IX, copper protoporphyrin, tetraphenylporphine tetrasulfonate, ATX-70, ATX-S10, pheophorbide-a, CIA1-phtalocyanine tetrasulfonate, and chlorine PAD-S31), tenoxicam, piroxicam, rose bengal, erythrosine B, merocyanine 540, dimethylformamide, cytosine arabinoside, pyridoxarbazole, 2,2'-azobis(2-amdinopropane), 5,5'-dimethyl-1-pyrroline-X-oxide, e-pyridyl-1-oxide-N-t-butylnitrone, and anti-cancer agents (e.g., nitrogen mustard, cyclophosmadmide, bleomycin, adriamycin, FAD104, amphotericin B, mitomycin C, daunomycin, cisplatin, etopside, diaziquone, dihydroxy(oxbi-guoanido) boron, and 5-fluorouracil) (See e.g., Rosenthal et al., Ultrasonics Sonochemistry 11 (2004) 349; herein incorporated by reference in it entirety).

In some embodiments, toxic agents comprise agents that induce or stimulate apoptosis. Agents that induce apoptosis include, but are not limited to, radiation (e.g., X-rays, gamma rays, UV); tumor-derived growth factor ligands, receptors, and analogs; kinase inhibitors (e.g., epidermal growth factor receptor (EGFR) kinase inhibitor, vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); antisense molecules; antibodies (e.g., HERCEPTIN, RITUXAN, ZEVALIN, BEXXAR, and AVASTIN); anti-estrogens (e.g., raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine, dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

Alkylating agents suitable for use in the present compositions and methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (dimethyltriazenoimid-azolecarboxamide).

In some embodiments, antimetabolites suitable for use in the present compositions and methods include, but are not limited to: 1) folic acid analogs (e.g., methotrexate (amethopterin)); 2) pyrimidine analogs (e.g., fluorouracil (5-fluorouracil), floxuridine (fluorode-oxyuridine), and cytarabine (cytosine arabinoside)); and 3) purine analogs (e.g., mercaptopurine (6-mercaptopurine), thioguanine (6-thioguanine), and pentostatin (2'-deoxycoformycin)).

In still further embodiments, chemotherapeutic agents suitable for use in the compositions and methods of the present invention include, but are not limited to: 1) vinca alkaloids (e.g., vinblastine, vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin and carboplatin); 7) anthracenediones (e.g., mitoxantrone); 8) substituted ureas (e.g., hydroxyurea); 9) methylhydrazine derivatives (e.g., procarbazine (N-methylhydrazine)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

In some embodiments, nanoparticles include additional agents for imaging purposes. In some embodiments, the imaging agent is, for example, selected from magnetic materials (e.g., iron for MRI); proteins that catalyze luminescent reactions (e.g., luciferins such as luciferase for bioluminescent imaging); fluorescent dyes (e.g., rodamine or fluorescein isothiocyanate for fluorescent imaging); fluorescent proteins (e.g., green fluorescent protein); and radioactive elements (e.g., for autoradiography).

In some embodiments, nanoparticles comprises nanomaterials to be used as a contrast agent for X-ray/CT, or MRI utilizes photoactive properties, absorbance for X-rays or paramagnetic properties for T1 magnetic resonance imaging. Exemplary contrast agents include, but are not limited to, Gadolium contrast agents, fluorescent agents (e.g., Alizarin Red S), and contrast agents described in U.S. Pat. No. 7,412,279 or 6,540,981, each of which is herein incorporated by reference in its entirety.

D. Activators

Embodiments of the present invention provide activators that activate the toxic agent, leading to local cellular and tissue damage in cardiac cells in a cell specific manner. The present invention is not limited to a particular activator. Any activator that activates the toxic agent finds use in embodiments of the present invention. In general, activators provide a source of energy that results in the toxic agent releasing energy (e.g., in the form of free radicals) that leads to cell death or ablation. Examplary activators include, but are not limited to, light, heat, radiation, sound, and the like.

In some embodiments, the present invention is illustrated using photodynamic therapy. However, the present invention is not limited to the use of photodynamic therapy. One of skill in the art recognizes that a variety of toxic agents and activating systems finds use in embodiments of the present invention.

Figure 2:
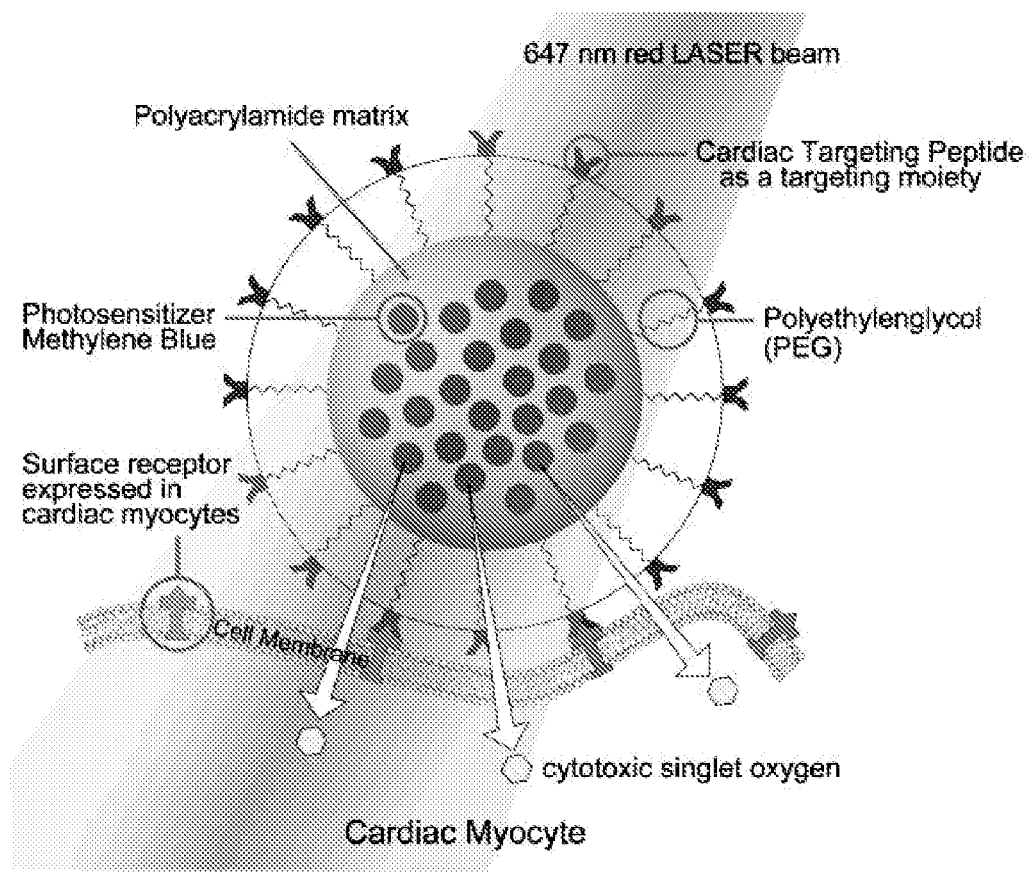
FIG. 2 shows a schematic of nanoparticles of embodiments of the present invention.

Photodynamic therapy (PDT) comprises use of a chemical reaction whereby a photosensitizer is activated by light energy and releases reactive oxygen species (Yang et al., Lasers in Surgery and Medicine 2010; 42:671-679) (FIG. 1). PDT includes two stages. First, the photosensitizing agent is administered and accumulates on or in the tissue by passive or active targeting. Then, the photosensitized tissue is exposed to light at a wavelength that coincides with the absorption spectrum of the photosensitizing agent which, upon illumination, becomes excited. With photodynamically efficient photosensitizers, this leads to an energy transfer to molecular oxygen (available in cells) and to the generation of reactive oxygen species (ROS), mainly singlet oxygen ($O_2$). The subsequent oxidation of the cell's lipids, amino-acids and proteins induces necrosis and/or apoptosis of the tissue. As ROS, due to an extremely limited lifetime and diffusion length, have a much localized toxicity, their release leads to irreversible but exquisitely restricted cellular damage and tissue necrosis. Thus the damage induced by PDT is confined to the cells that have been photosensitized, while adjacent non-photosensitized cells remain unaffected (Dolmans et al., Nature Reviews Cancer 2003; 3:380-387). The recent development of nanoplatforms has enabled conjugating photosensitizers as well as targeting moieties to hydrogels in such a way that targeted, cell-specific PDT has been made available for a variety of applications (Dolmans et al., Nature Reviews Cancer 2003; 3:380-387; Ross et al., 2004; Suci et al., Langmuir 2007; 23:12280-12286; Couleaud et al., Nanoscale 2010; 2:1083-1095; Chen et al., Critical reviews in eukaryotic gene expression 2006; 16:279). However, the efficiency of implementing nanoplatform-enabling PDT to target specifically a cardiac cell population has not been achieved. Experiments conducted during the course of development of embodiments of the present invention provide a targeted cardiac ablation technology that achieves nearly complete cell and spatial specificity. This method includes myocyte-specific targeted delivery of photodynamic therapy (PDT)-enabled nanoparticle platforms (NPs). The cell type selectivity is achieved through conjugation of a myocyte-specific target agent-cardiac targeting peptide (CTP) (See e.g., Zahid et al., PloS one 2010; 5:e12252) onto the NP's surface (FIG. 2). In addition, the spatial specificity is achieved by photodynamic ablation that enables local confinement of the therapeutic effect, minimizing adverse damage to adjacent non-targeted cells and tissues.

Experiments conducted during the course of development of embodiments of the present invention demonstrated a cell- and spatially-specific ablation methodology encompassing the synergistic implementation of two agents, both conjugated with a biodegradable nanoparticle: a myocyte-targeting peptide (e.g., CTP), and a photodynamic therapy enabling photosensitizer (e.g., methylene blue).

Figure 5:
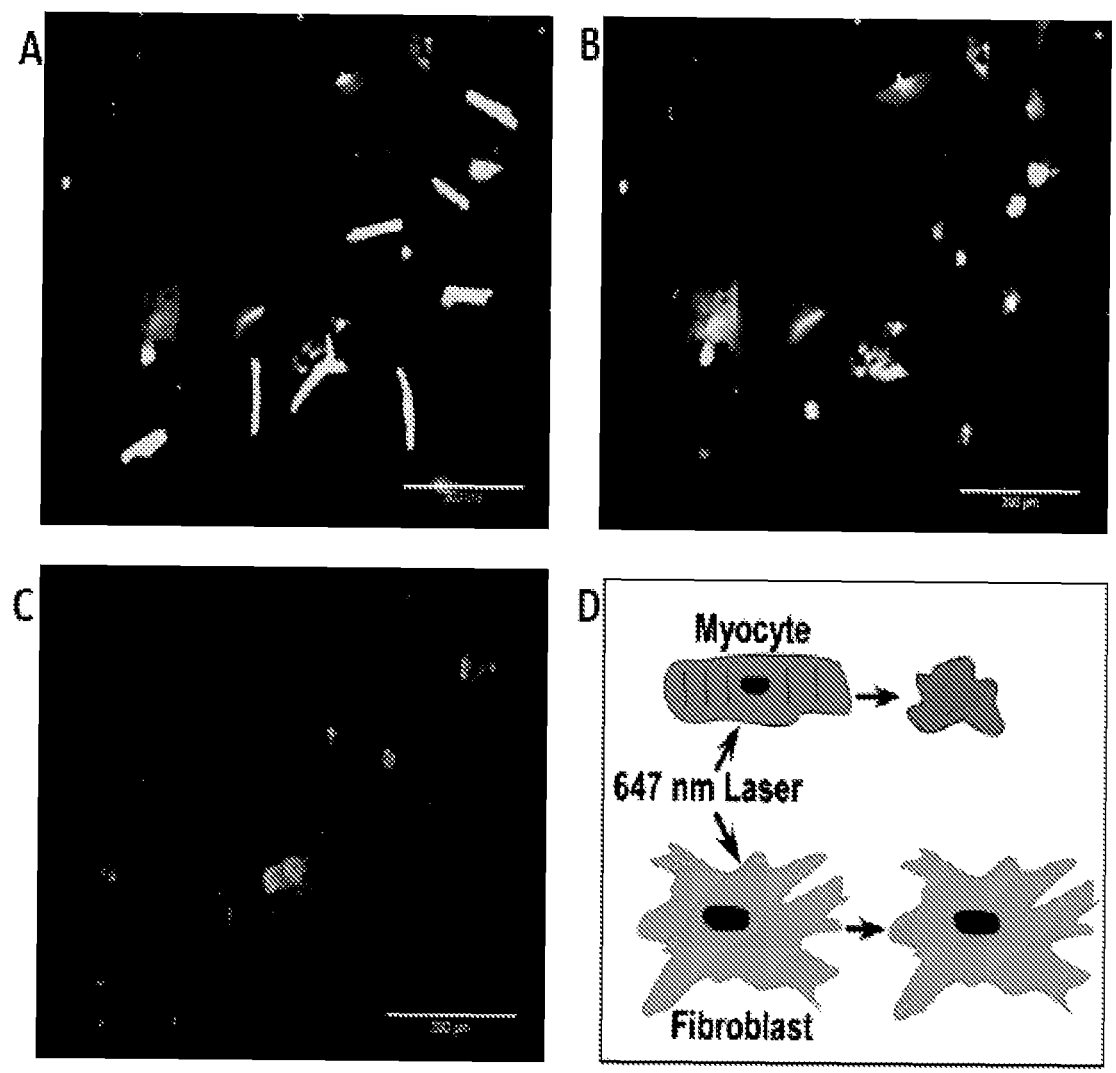
FIG. 5 shows myocyte-specific ablation by CTP targeted-NPs. (A) Co-culture of adult rat ventricular myocytes (rod shaped) and fibroblasts (flat irregular shape) before illumination and after illumination (B), showing significant morphological changes, and PI uptakes in myocytes only. (C) Confocal fluorescence image showing the selective binding of targeted-NPs to only myocytes. (D) Schematic showing that only myocytes underwent cell death after targeted PDT.

It was demonstrated that targeting nanoparticles have the unique capability to specifically attach to myocytes, and not to fibroblasts, and to induce cell-specific death upon local Laser light delivery, followed by local release of ROS. This is exemplified by the markedly decreased number of viable myocytes in the areas illuminated, while the number of healthy fibroblasts stays constant after illumination (FIG. 5). This cell selective therapy approach, finds use in overcoming current limitations of cardiac ablation.

In some embodiments, the activator is sound (e.g., sonodynamic therapy; See e.g., Rosenthal et al., supra, herein incorporated by reference in its entirety). Sonodynamic therapy is the ultrasound dependent enhancement of cytotoxic activities of certain compounds (sonosensitizers). Ultrasound is a mechanical wave with periodic vibrations of particles in a continuous, elastic medium at frequencies equal to or greater than 20 kHz. In liquids, its velocity of about 1000-1600 m/s translates into the wavelength range from micrometers to centimeters. Consequently the acoustic field cannot couple directly with the energy levels of molecules, including the biological milieu at the molecular level. Therefore, this radiation is not only perceived as safe, but has a very good tissue penetrating ability without major attenuation of its energy. In some embodiments, sound is generated outside of the body and targeted through tissue to the desired treatment region.

Sonodynamic therapy is based on the synergistic effect of ultrasound and a chemical compound referred to as "sonosensitizer". The effect can be localized by focusing the ultrasound on a defined region (e.g., regions of cardiac tissue). In some embodiments, ultrasound is delivered transdermally to a specific region of cardiac tissue.

In some embodiments, activators are pharmaceutical agents that activate therapeutic agents (e.g., chemotherapeutic agents). For example, in some embodiments, verapamil is used to active or improve efficacy of chemotherapeutic agents (e.g., doxorubicin).

E. Systems

Embodiments of the present invention provide compositions, kits, and systems comprising the nanoparticles described herein. In some embodiments, systems comprise nanoparticles and instruments or apparatuses for delivering the activator (e.g., laser, ultrasound apparatus, radiation delivery apparatus and the like). In some embodiments, systems further comprise instruments for imaging nanoparticles in cardiac tissue and computer systems to control delivery of activators, imaging, data analysis, and data display.

II. Uses

The nanoparticles described herein find use in a variety of therapeutic, research, screening, diagnostic, and clinical applications. Exemplary uses are described herein.

A. Therapeutic Uses

In some embodiments, the present invention provides systems and methods for cardiac ablation therapy. For example, in some embodiments, nanoparticles are targeted to myocytes (e.g., using CTP). In some embodiments, nanoparticles are administered intravenously.

Cell-specific death is then induced upon local delivery of activator (e.g., laser light or sound) delivery (e.g., via the toxic agent embedded or on the surface of the nanoparticle), followed by local release of ROS. In such embodiments, myocytes are specifically targeted and killed only in the areas where activator is delivery, while the number of untargeted cardiac cells (e.g., fibroblasts) stays constant after delivery of the activator.

The present invention is not limited to a particular method of delivery of activator. In some embodiments, activator is delivered directly to the areas of the heart in need of therapy (e.g., as previously determined or determined using the diagnostic methods described below) via open heart surgery. In some embodiments, activators are targeted and controlled using automated systems (e.g., computer controlled).

In some embodiments, activators are delivered locally to the areas of the heart in need of treatment using a catheter or other intravenous or intraarterial delivery or transdermally (e.g., via ultrasound). Such methods avoid the need for open heart surgery.

In some embodiments, therapy is sonodynamic therapy. Sonodynamic therapy has the advantage of transdermal delivery, thus allowing the entire procedure to be conducted without invasive means. The toxic agent (e.g., sonosensitizer) is delivered (e.g., intravenously) and then targeted areas of cardiac tissue are treated with ultrasound.

In some embodiments, therapy is photodynamic therapy. Photodynamic therapy has the ability to bring spatial specificity, as only the areas illuminated are receiving therapy, while other regions remain untreated. The only study to have implemented PDT for cardiac ablation is the one by Ito A, et. al., in which the authors used talaporfin sodium as a photosensitizer agent injected intravenously in rats to demonstrate that electrical conduction blocks may be created upon epicardial illumination (Ito et al., IEEE Transactions on 2010; 57:488-495). However, it should be noted that, in that study, PDT was not targeted and damage likely occurred in all cardiac cell types in the region illuminated. In addition, the fact that talaporfin non-specifically binds to all organs, including the skin, hampers clinical applicability, as talaporfin skin deposition may lead to sunburns under subsequent sun exposure (Hettiaratchy et al., BMJ 2000; 320: 1245; D'hallewin et al., Lasers in Medical Science 1990; 5:13-15). In comparison, experiments described herein demonstrated that PDT with CTP-MB-NPs allowed one to selectively induce myocyte cell death without damaging adjacent fibroblast cells, even when the latter were at a nearly zero-distance from dying myocytes. The methods of embodiments of the present invention are advantageous over current ablation energies, which induce damage to myocytes as well as to bystander cells such as fibroblasts, adipocytes or neurons (Shah et al., J Am Coll Cardiol 2005 Jul. 19, 2005; 46:327-330), resulting in post-ablation complications.

In some embodiments, therapeutic methods treat cardiac arrhythmias (e.g., atrial fibrulation, premature atrial contractions, wandering atrial pacemaker, multifocal atrial tachycardia, atrial flutter, supraventricular tachycardia, tachycardia, junctional rhythm, junctional tachycardia, premature junctional contraction, premature ventricular contractions, accelerated idioventricular rhythm, monomorphic ventricular tachycardia, polymorphic ventricular tachycardia, ventricular fibrillation, heart blocks, long QT syndrome, Brugada syndrome, catecholaminergic polymorphic ventricular tachycardia, right ventricular dysplasia and abnormal Purkinje potentials leading to ventricular arrhythmias including electrical storms).

In some embodiments, therapies target and ablate or kill myocytes. However, the present invention is not limited to the targeting of myocytes. An advantage of implementing therapeutic nanoplatforms is the high versatility of these carriers to be conjugated to various optional targeting agents, for distinct cardiac ablation applications. In fact, any other targeting moieties (e.g., antibodies, peptides, etc.), functional dyes or bioactive agents can be readily implemented with these nanoplatforms (Orringer et al., Neurosurgery 2010; 66:736; Winer et al., Cancer research 2010; 70:8674; Hah et al., Macromol Biosci 2010 Oct. 25, 2010). Thus, targeting moieties specific to adult human cardiac fibroblasts and to other human cardiac cell types (Purkinje cells, cardiac neurons, adipocytes) known involved in cardiac arrhythmias perpetuation find use in embodiments of the present invention. For example, in some embodiments, cell-specific ablation of Purkinje cells while common cardiac myocytes are spared, is utilized. Purkinje potentials from the Purkinje network and have been shown to enable perpetuation of ventricular arrhythmias, in particular the ones involved in electrical storms (Aiba et al., Pacing and clinical electrophysiology 2001; 24:333-344; Nogami et al., Journal of the American College of Cardiology 2000; 36:811-823; Weerasooriya et al., Herz 2003; 28:598-606; Kohsaka et al., Pacing and clinical electrophysiology 2007; 30:701-704).

A similar approach finds use in the delivery of antiarrhythmic drugs in a cell-specific manner. As an example, ventricular pro-arrhythmic effects of common anti-arrhythmic drugs represent a major limitation of atrial fibrillation management (Podrid P J Curr Cardiol Rep 1999 November 1999; 1:289-296; Naccarelli et al., J Interv Card Electrophysiol 2003 October 2003; 9:215-222), and atrial-specific pharmacological agents are highly desirable (Vos M A. Journal of cardiovascular electrophysiology 2004; 15:1451-1452; Blaauw et al., Cardiovascular research 2007; 75:89). Targeted biodegradable nanoparticles which release drugs upon illumination (Vasir et al., Cold Spring Harbor Protocols 2010; 2008:pdb. prot4888; Shum et al., Advanced drug delivery reviews 2001; 53:273-284; Cheng et al., Journal of the American Chemical Society 2008; 130:10643-10647) can be implemented so to release an anti-arrhythmic drug to a specific cardiac type. Such highly selective drug administration drastically reduce the global dose, and thus any potential side effects.

In some embodiments, therapeutic uses described herein are used in conjunction with existing therapies or as a replacement for existing therapies. In some embodiments, nanoparticle-based therapeutics are used as a follow-up to failed or incomplete therapy (e.g., non-nanoparticle therapies).

B. Diagnostic Uses

In some embodiments, nanoparticles are utilized in imaging (e.g., in vivo imaging) applications. In some embodiments, a photosensitive agent (e.g., MB) or particle that is also fluorescent or otherwise imagible is utilized.

In other embodiments, nanoparticles further comprise separate imaging agents. For example, as described herein, in some embodiments, nanoparticles comprise contrast agent for imaging (e.g., X-Ray, computer tomography (CT) imaging, PET imaging, ultrasound, photo-acoustic imaging, or MRI imaging). For example, in some embodiments, $^{157}$Gd, gold, iodine, iron-oxide, or other suitable agent for use in imaging coat nanoparticles.

In some embodiments, nanoparticles are used to detect biological targets in vivo or in vitro by bioluminescent imaging. In some embodiments, nanoparticles comprise an enzyme that catalyzes a bioluminescent reaction. Enzymes that catalyze bioluminescent reactions include, but are not limited to, the following luciferases: bacterial luciferase (U.S. Pat. No. 4,548,994), *Photinus pyralis* luciferase (U.S. Pat. Nos. 5,670,356 and 5,674,713), *Renilla reniformus* luciferase, *Pyrophorus plagiophthalamus* luciferase, *Luciola cruciata* luciferase (Masuda et al., Gene 77:265-70 [1989]), *Luciola lateralis* luciferase (Tatsumi et al., Biochim. Biophys Acta 1131:161-65 [1992]), and *Latia neritoides* luciferase. The foregoing publications are specifically incorporated herein by reference.

In some embodiments, the imaging is performed in situ (See e.g., Contag et al., Nature Med. 4(2):245-47 [1998], incorporated herein by reference). Nanoparticles containing the bioluminescent enzyme are provided to the animal intravenously and allowed time so that the molecular recognition element binds to its biological target. In some embodiments, a substrate (e.g., bacterial or insect luciferin) for the bioluminescent enzyme is then provided (e.g., via intravenous, intraperitoneal, intravesical, or intracerebrovascular delivery) to the animal. In some embodiments, production of bioluminescence by the action of the enzyme on the substrate is then detected by a bioluminescence detection system. In some embodiments, the bioluminescence detection system comprises a Hamamatsu intensified CCD (ICCD, model C2400-32). In other embodiments, the bioluminescence detection system further comprises other devices for intensifying weak signals (e.g., microchannel plate intensifiers and devices for Peltier or liquid nitrogen cooling of the detector and/or intensifier). In some preferred embodiments, a grey scale image of the animal is obtained by opening the door of dark chamber in which the animal is placed. The door is then shut and the gain on the intensifier adjusted to maximum to detect the bioluminescent signal. The signal is then overlaid with the greyscale image in pseudocolor.

In other embodiments, nanoparticles are used to detect biological targets by magnetic resonance imaging (MRI). In some embodiments, the biological target imaged is in situ (See e.g., Ross et al., PNAS 95:7012-17 [1998]). Nanoparticles comprising the magnetic material are provided to the animal (e.g., intravenously) and time allowed so that the molecular recognition element binds to its biological target. In some embodiments, the biological target is then imaged with a magnetic resonance system (e.g., a 7-Tesla Magnetic Resonance System). In some embodiments, T1-weighted or T2-weighted images are obtained.

In some embodiments, diagnostic and imaging applications are performed in combination with therapeutic applications. For example, in some embodiments, imaging agents are utilized to visualize cardiac tissue before and after photodynamic therapy to monitor cell death. For example, in some embodiments, imaging allows a clinican to see where nanoparticles are bound (e.g., before, during or after activation). In some embodiments, imaging is used to visualize cardiac tissue after treatment to determine the extent or localization of cell killing. Thus, the imaging allows real time monitoring of the progress of the ablation therapy.

In some embodiments, imaging methods are utilized to determine a treatment course of activation. For example, in some embodiments, imaging is used after treatment to determine if additional treatment is needed in the form of, for example, additional activator in the same or different regions or delivery of additional nanoparticles.

In some embodiments, nanoparticles are used in research (e.g., imaging in animal models, structural studies, DNA-protein binding interactions, protein capture, etc.), during surgery, or drug screening applications.

EXPERIMENTAL

The following examples are provided in order to demonstrate and further illustrate certain preferred embodiments and aspects of the present invention and are not to be construed as limiting the scope thereof.

Example 1

Methods

Synthesis of Methylene Blue (MB) incorporated polyacrylamide (PAA) nanoparticles and Characterization has been done as detailed previously (Hah et al., Macromolecular bioscience 2011). CTP has the sequence APWHLSSQYSRT to which cysteine (C) was added to the end while synthesizing in order to conjugate with MB PAA NPs. Its phototoxic capability is determined as previously reported (Hah et al., supra).

Extraction of Primary Cardiac Myocytes and Fibroblasts and Co-Culture:

Adult rat ventricular myocytes and fibroblasts were isolated as detailed previously (Vaidyanathan et al., Journal of Biological Chemistry 2010; 285:28000-28009; Gustafsson et al., Mol Pharmacol December 2000; 58:1470-1478. All animal experiments were approved by the Unit for Animal Laboratory Medicine (ULAM) of the University of Michigan.

In Vitro PDT with Non-Targeted MB PAA NPs for PDT Susceptibility and in Vitro PDT with CTP Conjugated MB PAA NPs for Cell Type Specific Therapeutic Efficacy:

Non-targeted MB PAA NPs was added to the co-culture of adult rat ventricular myocytes and fibroblasts, adjusting the final NP concentration to 0.5 mg/mL. The 647 nm laser was irradiated to the cell specimen in the presence of live/death indicator reagents, calcein acetoxymethyl ester (Calcein AM, ex/em: 488/525 nm) for live cells and propidium iodide (PI, ex/em: 568/600 nm) for dead cells for 30 minutes and the cell viability was monitored in one minute interval. The mechanisms by which these indicators work is described previously (Kaneshiro et al., Journal of microbiological methods 1993; 17:1-16). Briefly, Calcein AM after crossing the cell membrane, the cytoplasmic esterase removes the acetomethoxy group and as a result it gets locked inside the cell and accumulated, emitting strong green fluorescence. When the cell dies, as the integrity of plasma membrane is disrupted, Calcein escapes out and stops emitting fluorescence. On the other hand, PI stains nucleic acids (DNA, RNA) in the cell and emits amplified red fluorescence. Cell membrane is not permeable to hydrophilic PI and only dead cells allow the entry of PI. Thereafter PI stains nucleic acids and emits fluorescence.

For CTP conjugated MB PAA NPs, the NPs were incubated with the co-culture at 0.5 mg/mL for 1 hour and the unbound NPs were removed by gentle washing with fresh cell media 3 times. The rest of procedures were same as non-targeted MB PAA NPs. The PDT experiments were performed with Olympus IX-70 microscopy equipped with Perkin Elmer Ultra view confocal imaging system using argon-krypton laser light source.

Results

Polyacrylamide (PAA) nanoparticles that were covalently linked with a photosensitizer, methylene blue (MB), thus called MB PAA NP (Hah et al., supra), and surface conjugated with polyethylene glycol (PEG) and a myocyte-specific targeting moiety, CTP (FIG. 2) were utilized. The MB covalently incorporated NPs were prepared following a previously reported method (as detailed above). The covalent linkage of MB to the NP matrix advantageously prevents MB dimerization, which would interrupt energy transfer from MB to oxygen to generate $^1O_2$ (Severino et al., Photochem Photobiol 2003 May 2003; 77:459-468). It also prevents the undesired action of enzymes, such as reductases, which would lead to a reduction of MB to the photo-inactive leuco-isomer form (Winer et al., Cancer research 2010; 70:8674), and it also prevents the leaching of MB out of the NP.

Figure 3:
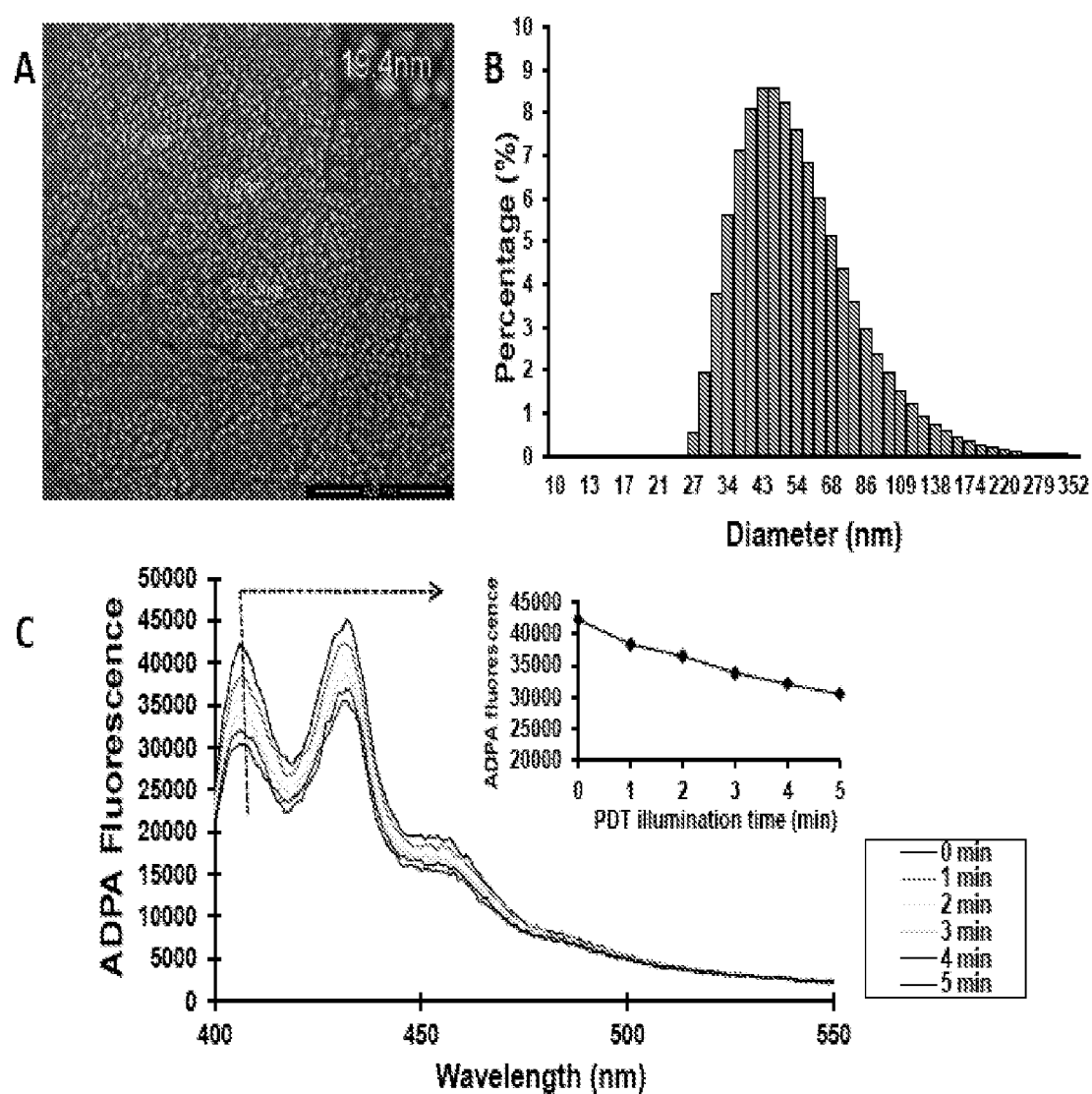
FIG. 3 shows (A) Scanning Electron Microscopy (SEM) imaging in dry phase showing homogeneous NP size distribution. (B) Dynamic light scattering showing NP size distribution (DLS) in wet phase. (C) Singlet oxygen generation. The CTP-conjugated MB PAA NPs exhibited a reduction in fluorescence of ADPA at a wavelength of 410 nm as shown by the dotted arrow, indicating the generation of singlet oxygen during continuous illumination at 647 nm.

The size of the produced particles was determined by two methods: Scanning Electron Microscopy (SEM) imaging, in the dry phase, and dynamic light scattering (DLS), in the wet phase. The SEM showed a nearly homogeneous size distribution around a diameter of 20 nm (FIG. 3A), while the hydrodynamic diameter determined by DLS showed a distribution around 50 nm, as depicted in the NP size histogram (FIG. 3B). The fact that the PAA nanoparticles exhibited a swelled-up size in the wet phase, in comparison with the dry phase, is a characteristic of hydrogels. The photodynamic efficacy was confirmed by measuring $^1O_2$ production with a $^1O_2$ sensitive fluorescent probe, anthracene-9,10-dipropionic acid (ADPA) (Weerasooriya et al., Herz 2003; 28:598-606). The MB PAA NPs exhibited a reduction in ADPA fluorescence intensity, with a rate constant of $k=0.064\ s^{-1}$, indicating the generation of singlet oxygen during continuous illumination at 647 nm (FIG. 3C).

Figure 4:
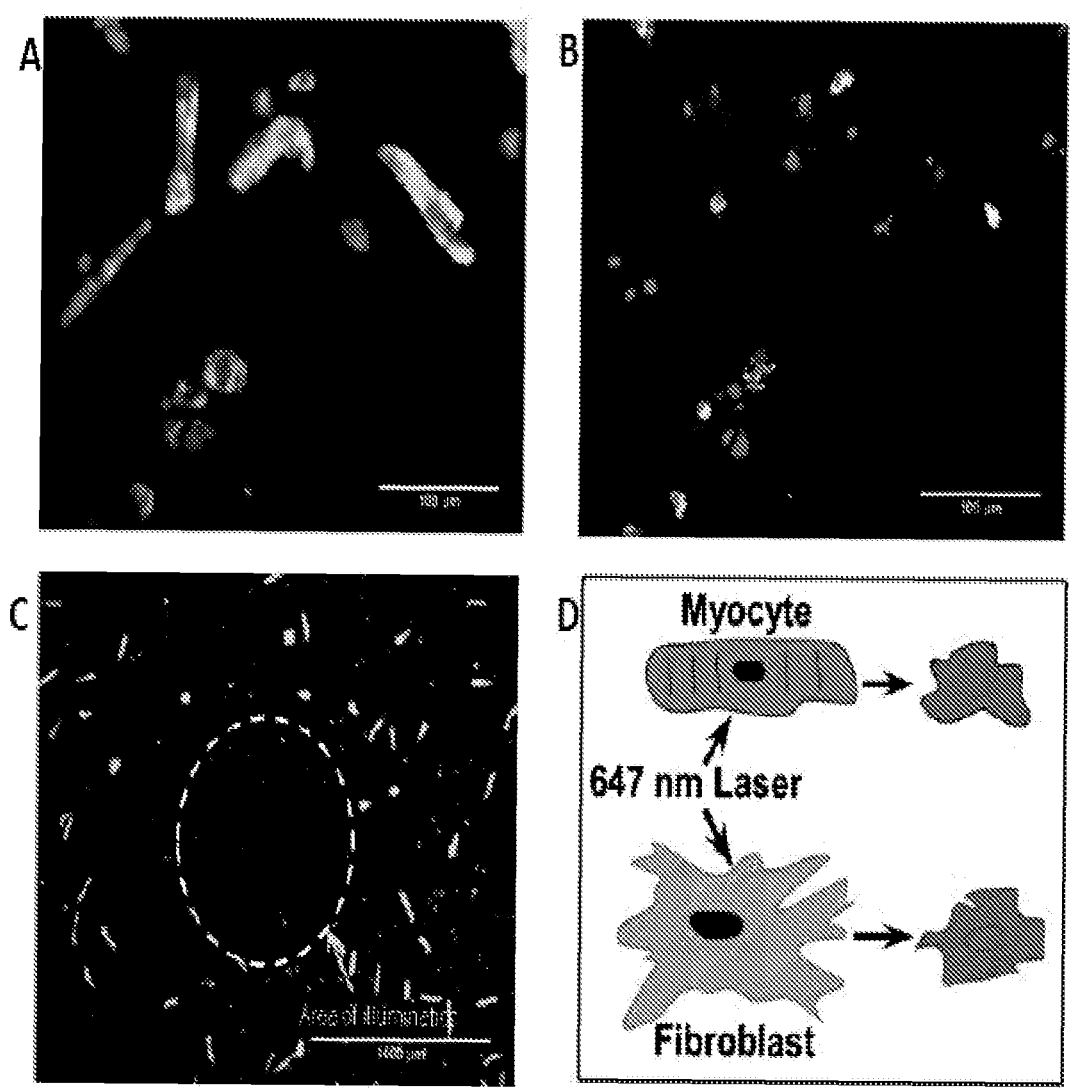
FIG. 4 shows susceptibility of cardiac cells to PDT (Non targeted PDT). (A) Co-culture of adult rat ventricular myocytes (rod shaped) and fibroblasts (flat irregular shape) before illumination and after illumination (B) showing significant morphological changes and PI uptake are seen in both cell types. (C) View of the area of illumination (circled area) illustrating that both cell types received PDT. (D) Schematic showing that both cell types underwent cell death after non-targeted PDT.
Figure 6:
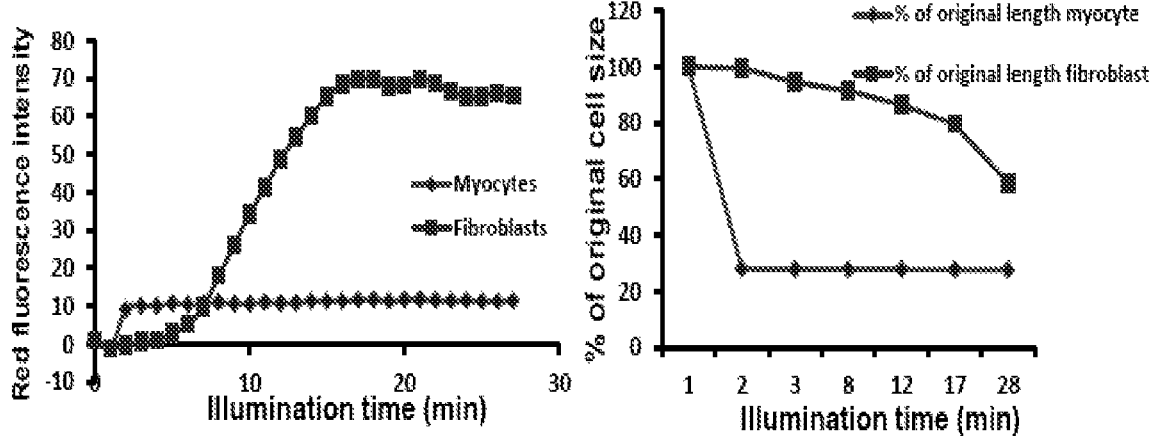
FIG. 6 shows quantification of PI fluorescence uptake and cell size changes. (A) Non-targeted PDT experiment: Both cell types exhibited a progressive increase in PI fluorescence uptake (left panel), and a decrease in cell size (right panel). (B) Targeted-PDT experiment: Fibroblasts were unaffected while myocytes showed PI uptake (left panel) and decrease in cell size (right panel).
Figure 6:
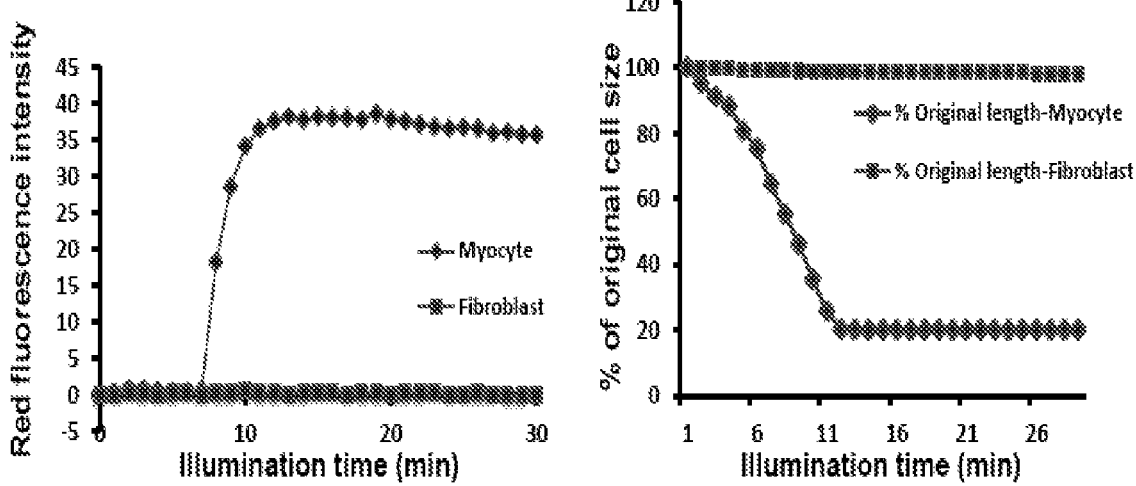

In vitro experiments were conducted in co-cultured isolated adult rat ventricular myocytes and fibroblasts: first, to establish the feasibility of our approach that cardiac cells (both myocytes and fibroblasts) are susceptible to PDT and second, to show if PDT-NPs could be selectively delivered to the cardiac myocytes, resulting in myocyte selective dell death. In the first set of cellular experiments, cells were treated by PDT in a medium containing 0.5 mg/mL non-targeted MB PAA NPs (meaning NPs without CTP) in the presence of live/death indicator reagents, Calcein AM for live cells and propidium iodide (PI) for dead cells. Upon illumination with a weak 647 nm laser beam (1 mm in diameter, 500 µW), the myocytes exhibited rapid morphological changes from a rod-like shape to a random shrunken shape (after 1 min) while the fibroblasts showed slightly delayed morphological changes (after 5 min) and, yet, both cell types exhibited progressively increasing PI uptake (fluorescence) and vanishing calcein staining, indicating cell death (FIGS. 4A, 4B, and 6A). This observation showed that both myocytes and fibroblasts are sensitive to the oxidative damage by PDT, as both cell types rapidly experienced cell death after illumination. Importantly, cell death was only observed inside the illuminated region (FIG. 4C), evidencing that the cell death was indeed from PDT.

In a different set of experiments, the CTP conjugated MB-PAA NPs were incubated with the adult rat ventricular myocyte and fibroblast co-culture for 1 hour and then unbound NPs were washed out thoroughly. PDT was again performed by illuminating an about 1 mm diameter area with a 647 nm red laser (500 µW) for about 30 minutes, in the presence of live/dead indicator reagents (see above). During this time period, the myocytes progressively exhibited morphological changes, and showed uptake of PI, a dead cell indicator, as well as a progressive loss of Calcein-AM, a live cell indicator. On the other side, while all myocytes exhibited major changes, leading to rapid cell death, none of the cardiac fibroblasts were affected, indicating that this targeted PDT achieved nearly complete cell specificity (FIGS. 5A, 5B and 6B). The binding of CTP conjugated MB PAA NPs to myocytes was easily confirmed by imaging the fluorescence of MB dye within NPs (FIG. 5C). In contrast, negligible binding towards the fibroblasts was detected.

Note that while the excitation maximum of the MB PAA NP is around 665 nm, a sharp line width, 647 nm laser light was used (because of limitations in the laser optics setup). Thus, it is likely that the PDT efficiency would have increased or that the required illumination time would have been briefer or an even weaker light source would have sufficed, if an optimal wavelength light source had been employed.

Example 2

In Vivo Experiments

In vivo experiments are done to test myocyte specific PDT. Langendorff-perfused rat hearts are used to compare myocyte-specific ablation with non-specific ablation. Using optical mapping techniques, basic electrophysiological parameters (APD and impulse velocity) and re-entry dynamics before and after ablation are deternubed. It is contemplated that conjugating CTP to PDT-NPs obtains myocyte-specific ablation in Langendorff-perfused rat hearts and that non-ablated regions retain their baseline electrophysiological properties while they are fully insulated from the ablated region.

Preparation of Langendorff-perfused rat hearts: After anesthesia, rat hearts are removed and Langendorff-perfused with an oxygenated Krebs-Henseleit solution as previously (Ford et al., *British journal of pharmacology.* 2002; 135: 1191-1198) and within a 150 ml closed-loop recirculation system.

Cardiac targeting peptide (CTP) synthesis: The published sequence of CTP, APWHLSSQYSRT is used to generate 100 mg.

Preparation of CTP-PDT-NPs: The CTP includes cysteine on one end, which is conjugated to MB-incorporated PAA NPs using a two-step reaction, as often done before. First, the surface of the MB-incorporated PAA NPs (Hah et al., *Macromolecular bioscience.* 2011), which contains primary amine groups (—NH$_2$), are conjugated with the PEG cross-linker (succinimidyl ester-PEG-maleimidyl ester), based on NH$_2$—NHS reactivity. Then, cys-terminated CTP is conjugated to the MAL terminal of the PEG chain, based on SH-MAL reactivity. Then, an optimal amount of cys-terminated CTP is conjugated to the MAL terminal of the PEG chain, based on SH-MAL reactivity. The optimal amount of CTP per NP is determined as follows: MB NPs conjugated with various amount of CTPs are prepared and then isolated myocytes are treated with CTP-PDT-NPs with a 1 hour incubation period followed by washing off unbound NPs. Finally, myocyte fluorescence intensity at various CTP amount/NP are measured and compared.

Figure 7:
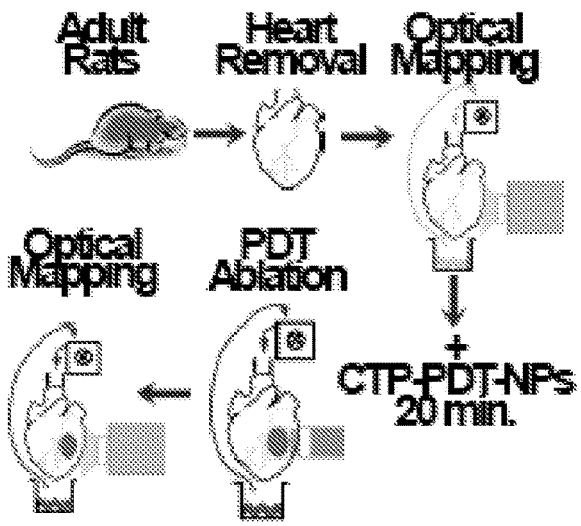
FIGS. 7A and B shows a schematic of in vivo targeting protocols.
Figure 7:
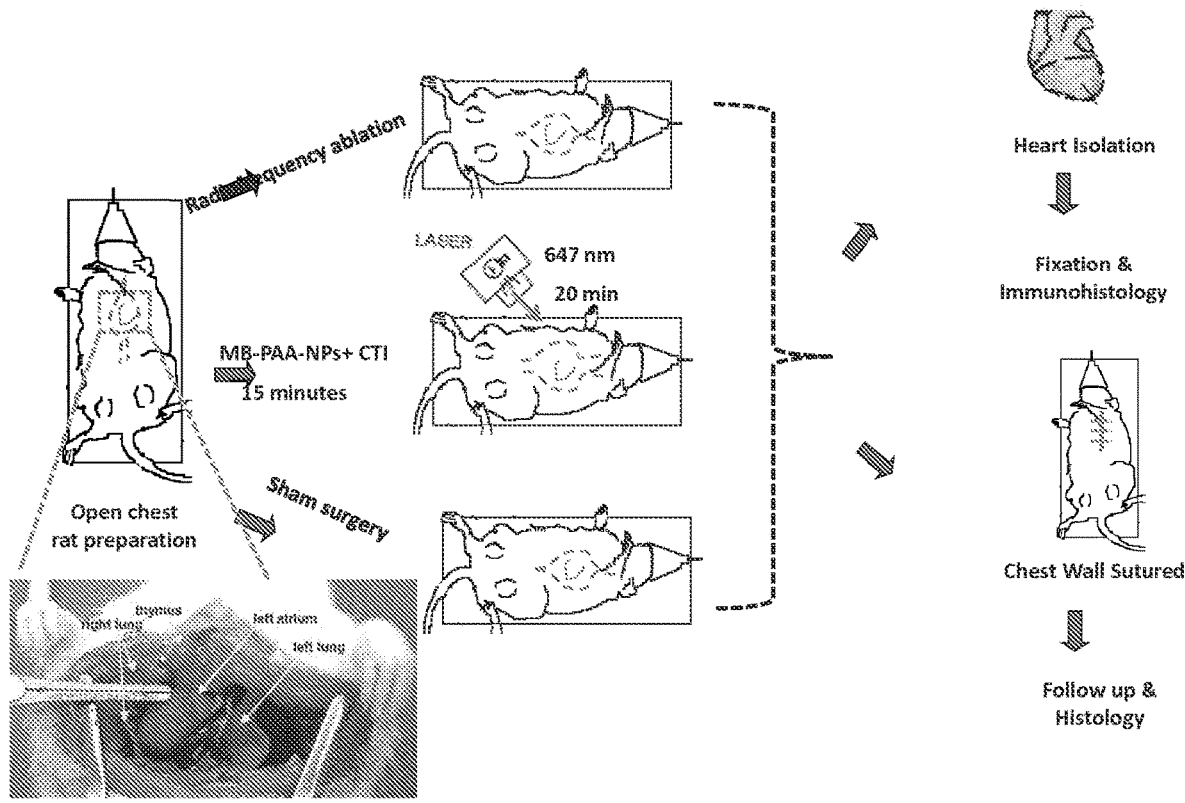

Experimental protocol: A summary of the experimental protocol is presented in FIG. 7A. On the day of experiment, adult rat hearts are removed and Langendorff-perfused as described above. After having perfused the excitation-contraction uncoupler blebbistatin (5-10 µM) to decrease contraction artifacts, and with Di-4-ANEPPS as a voltage-sensitive dye, as done previously (Fedorov et al., *Heart Rhythm.* 2007; 4:619-626; Pandit et al., *Cardiovascular Research.* 2011; 89:843), high resolution optical mapping is conducted, using a charge-coupled device camera. 5-second movies at 500 frames per second are obtained, during a pacing protocol at progressively shorter cycle length. Fibrillation is induced by burst pacing, and reentrant activities, as well as focal discharges, are recorded. After recording movies, targeted CTP-PDT-NPs are perfused for 20 minutes and a circular region of ablation is created on the anterior aspect of the left ventricle (see FIG. 7) by focusing a 671 nm wavelength laser beam (3 mm diameter, 500 mW-1 W) for 20 min. After illumination, optical movies are recorded during reentry and pacing (if needed defibrillation is obtained with a low energy external defibrillator). Depending on the results, longer or shorter illumination durations and various CTP-PDT-NPs concentrations are also tested.

Control experiments: In one control group (control 1), non-targeted, e.g., non-cell-specific PAA-MB-NPs ablation is performed. In another group (control 2), radiofrequency energy (40 W, 5 sec.) delivered with a 4-mm diameter radio-frequency catheter is used to generate another type of non-specific ablative lesion on the anterior aspect of the heart. In 2 additional groups (control 3 and 4), the impact of maintaining isolated hearts for the duration of an experiment and in the presence of laser light is performed. Control 3 group enables comparing movies before and after a one-hour waiting period in the absence of light and PAA-MB-NPs. Then, in another group (control 4) the possible effects of laser illumination on isolated hearts is investigated. 671 nm Laser light is directed at the hearts for 20 minutes, in the absence of NPs, and movies before and after illumination are compared.

Optical mapping movie analysis: Ensemble averaging at each pixel is performed over 5 or more propagating wavefronts synchronized with stimuli. Background fluorescence is subtracted from each frame, and spatial (3×3 pixels) and temporal (7 pixels) conical convolution filters are applied. Dominant frequency maps and phase maps are constructed. Optical APDs are measured at 80% repolarization. Also, the distributions of activation times (50% of upstroke) for the spatial regions of 5×5 pixels are fitted with the plane, and gradients of activation times gx and gy are calculated for each plane along the x and y axes, respectively. The magnitude of the local CV is calculated for each pixel as (gx2+gy2)−½. Mean values and standard deviations for CV and APD are calculated for the entire visible surfaces and for sequential activations. During pacing, wavelength (WL) is calculated as WL=APD×CV.

Determination of Cell Viability:

a. Live/Dead Indicators

The photodynamic effect of the CTP-PDT-NPs on cell viability is quantified using a commercial live/dead cell assay (Invitrogen, USA). The performed assay employs calcein acetoxymethyl (calcein AM) and propidium iodide (PI). Live cells have intracellular esterases that convert non-fluorescent, cell-permeable calcein AM (hydrophobic) to intensely fluorescent calcein (hydrophilic). The fluorescent cleaved calcein is retained within cells. In contrast, damaged cells have ruptured membranes which allow PI to enter these cells and bind to nucleic acids, diffusing calcien indicator out. Once bound to nucleic acids, PI produces a bright red fluorescence, seen only in cells with a damaged membrane, e.g., in damaged/dead cells. Thus, a calcein AM and PI mixture in PBS buffer is used to differentiate live cells (green) from dead cells (red). This mixture is added before the ablation and the change of fluorescence in cells is observed under confocal microscopy.

b. Characterization of Fibroblasts After Ablation

In the ablated and unablated region of heart samples, fibroblasts morphology is evaluated by DDR2 immunostaining (Baudino et al., *Microscopy and microanalysis.* 2008; 14:117-125). Fibroblast morphology changes indicative of cellular damage induced by ablation are evaluated.

Myocyte-Specific Ablation in an in Vivo Rat Open-Chest Preparation

PDT-NPs conjugated with the cardiac targeting peptide (CTP), which selectively binds to cardiac myocytes, is used. Myocyte-specific ablation CTP-PDT-NPs is compated with non-specific radiofrequency ablation.

Rat Open-Chest Preparation:

Rat open-chest preparations are obtained as described previously (Zacharowski et al., Open-chest models of acute myocardial ischemia and reperfusion. In: Dhein S, Mohr F, Delmar M, eds. *Practical methods in cardiovascular research.*: Springer; 2005: 39-40; Ito et al., *Biomedical Engineering, IEEE Transactions on.* 2010; 57:488-495; Ito et al., 2008: 4361-4363). Briefly, Sprague-Dawley rats (Charles River, Mass.), weighing 250 to 350 g are anesthetized with heparin, ketamine (100 mg/kg) and midazolam (3 mg/kg) intraperitoneally. A tracheostomy tube is inserted, and ventilatory support is provided with a small animal ventilator (Harvard Apparatus, South Natick, Mass.). ECG electrodes are positioned on the animal limbs and connected to an amplifier (Biopac System, Inc) in order to continuously monitor frontal ECG leads derivations. A 24-gauge angiocatheter is inserted percutaneously into a peripheral vein and ketamine (10 mg/kg/hr) and midazolam (0.3 mg/kg/hr) is infused continuously and adjusted to maintain surgical anesthesia. Polyethylene catheters (PE 50, Clay-Adams, Parsippany, N.J. and Radnoti octapolar 2-French electrophysiology catheter) is inserted surgically in the right internal jugular vein-for measurement of central venous pressure and recording of right ventricular intra-cardiac electrograms-, and in the left carotid artery for measurement of arterial pressure. After median thoracotomy, the chest is opened with the help of thoracic retractors.

Experimental Protocol

As depicted in FIG. 7B, three experimental groups are formed. In group 1 (n=10), after heart stabilization by the formation of a pericardial cradle (Zhang et al., *Journal of Huazhong University of Science and Technology. Yixue Yingdewen ban.* 2004; 24:309; Starr et al., *Am Heart J.* 1943; 26:724-732), radiofrequency energy is delivered at the apex of the left ventricle with a 4-mm-tip 7-French ablation catheter (15-40 W, 50° C., 1-5 minutes). Five animals are euthanized immediately after ablation and the heart is removed for histological analysis. In five animals, the chest wall is sutured and the rats followed-up for 4 weeks. In group 2 (n=10), PDT-NPs are employed to achieve cell-specific ablation. CTP-conjugated PAA-MB-NPs are prepared. PDT is performed with the optimized PDT parameters (See below) and CTP-PDT-NPs are injected intravenously through the tail vein. A 671 nm laser beam is shined onto the left ventricular apex. Five animals are euthanized at the conclusion of the experiment and the heart is removed for histological and cellular investigations, assessing the degree of damage induced to myocytes, and, in contrast, the extent to which non-myocyte cells are spared in the area of illumination (see below). In another 5 animals, the chest wall is sutured and animals are carefully monitored over 4 weeks. After 4 weeks, the hearts from these animals are probed as detailed below. In group 3 (n=5), a sham surgery procedure is performed. After obtaining an open-chest preparation the chest wall is sutured and the sham-operated animals are followed-up for 4 weeks.

Optimization of in Vivo PDT Parameters:

The NP dose and time interval between the NP injection and light illumination are optimized. The light dose of 180 J/cm2 is used, based on on-going in vivo PDT studies on a rat brain tumor model. Based on the in vivo toxicology studies showing that 10-500 mg of PAA NPs per kg of animal is safe, with no evidence of alterations in histopathology or clinical chemistry values (Koo et al., *Adv Drug Deliv Rev.* 2006; 58:1556-1577), the NP is injected with a dose of 100, 200, 300 and 400 mg/kg. In the experiments proposed, a portable 671 nm red diode laser system (Changchun Dragon Lasers Co., Ltd)—including a laser head with about 2 mm beam diameter connected with a diffuser tip, built-in SMA905 fiber connector with a coupled light guide, and a power supply-with tunable output power (0-1 W) is used. It is contemplated that it will take approximately 15 minutes for CTP to reach the heart (Zahid et al., *PloS one.* 2010; 5:e12252), and allowing for binding to myocytes, the delay time interval will vary from 10 min to 60 min.

Ventricular stimulation and EP mapping: In all groups, before the heart removal procedure, an epicardial stimulating electrode is positioned on the right ventricle and a stimulation protocol-ramp and S1-S2- is applied to elicit ventricular arrhythmias. In the eventuality of the initiation of episodes of sustained ventricular arrhythmia, external defibrillation (epicardial paddles, 2J, biphasic waveforms) is attempted to restore sinus rhythm. This inducibility is compared among all the groups. In order to confirm ablation EP mapping is performed before and after ablation as follows: Before PDT or radio-frequency ablation, bipolar ventricular electrograms are acquired at about 20 ventricular locations in the ablated region and its surroundings. After ablation, this mapping sequence is repeated and any decrease in local electrogram amplitude in the ablated region, as compared to surroundings is observed. The decrease in amplitude is quantified and a map of bipolar electrogram amplitudes is constructed in Matlab with an in-house algorithm. Alternatively, a sub-group of the ablated hearts is compared with sham-operated animals, with optical mapping techniques, in isolated, Langendorff-perfused hearts, as described above.

Data Analysis: (i) Immuno-histochemistry: In order to determine which cell type experienced cell death and in which proportion, a myocyte and fibroblast cell specific antibody staining, in samples from experimental groups 1, 2 and 3 (RF ablation, myocyte-specific ablation and sham-operated, respectively) is performed. The following cell-specific antibodies are implemented in the heart sections: fluorescein-phalloidin (green) for myocyte staining and fibroblast-specific receptor DDR2 (blue) for fibroblasts, as done previously (Baudino et al., *Microscopy and microanalysis.* 2008; 14:117-125).

(ii) Hematoxylin-eosin and picro-sirius staining: At the end of the experiments, the hearts are immersed in 10% neutral buffered formalin. The tissue samples are fixed in paraffin and sectioned every 4 μm with a microtome. The paraffin sections are stained with Hematoxylin-Eosin or picro-sirius stain, and observed with a light microscope. The ablation site and surrounding areas are analyzed, so as to determine the presence and extent of inflammatory and fibrosis infiltrates. (iii) Organ toxicity evaluation: Organs such as liver, kidneys, brain, as well as peri-cardiac structure such as diaphragm and esophagus, are collected. Hematoxylin-eosin and picro-sirius red staining of tissue slides are obtained to determine whether the injection of PDT-NPs led to extra-cardiac inflammation and fibrosis. The presence of inflammatory infiltrates (neutrophils, macrophages) or collagen deposition on histological sections are considered indirect markers of toxicity. (iv) Fibroblast proliferation assessment: Specific attention is paid to comparing the impact on fibroblast physiology of non-specific radio-frequency ablation with myocyte-specific PDT-NPs ablation. First, signs of differentiation into myofibroblasts are assessed with α-smooth-muscle actin staining. To assess fibroblasts proliferation, bromodeoxyuridine (BrdU, 100 mg/kg) is administered intraperitoneally 2 h before sacrificing and tissue samples are stained with anti-BrdU antibody as described previously (Walsh et al., *Cardiovascular research.* 2010; 86:365).

Example 3

In Vivo Demonstration of the Ability of Targeted Nanoplatforms to Cross Blood Vessel Endothelial Lining One of the major hurdles to successfully deliver nanoplatforms to any tissue type is to succeed in crossing the endothelial cell layer which separates blood vessels from surrounding structures. Previously, nanoplatforms were mostly designed for cancer tissue in which the endothelial lining is vastly different from the one present in cardiac tissue.

The platform comprises polyacrylamide (PAA) nanoparticles conjugated with a photosensitizer, methylene blue (MB)—or alternatively Rhodamine (Rh), a fluorescent probe- and a cardiac targeting peptide (CTP).

Figure 8:
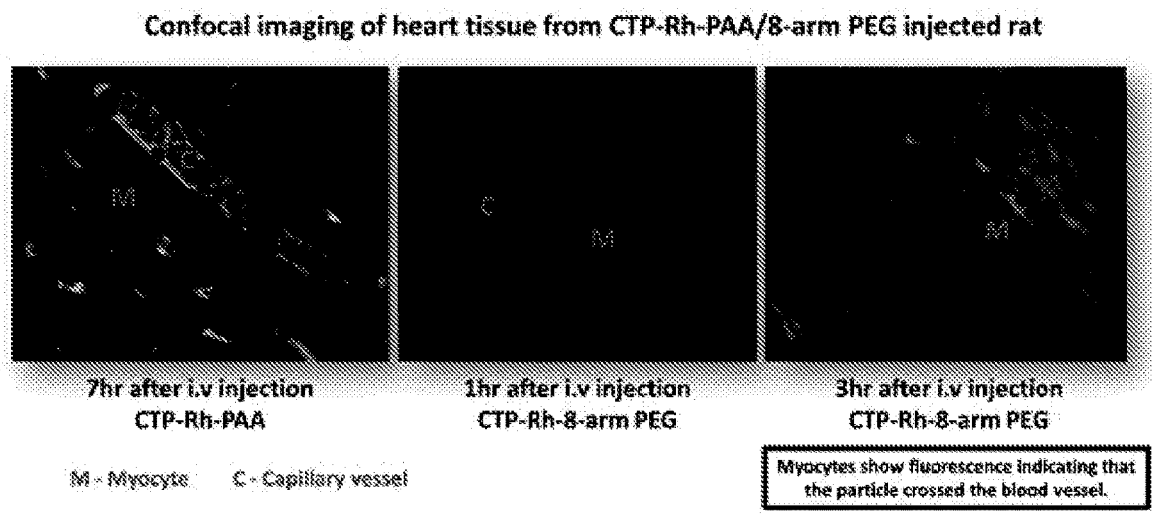
FIG. 8 shows targeting of PAA and PEG particles to cardiac cells.

In vivo CTP-MB-PAA testing started with injecting CTP-Rh-PAA NPs into the rat tail vein to subsequently collect heart tissue at either 1 or 3 hours post-injection. Confocal microscopy demonstrated that MB-PAA-CTP nanoplatforms remained in blood vessels and were not found in the cardiac cells (left panel of FIG. 8). After a detailed analysis, it was concluded that nanoparticle size was the main limiting factor in preventing blood vessel crossing.

The size of the nanoparticle was reduced from 50 nm to 10 nm. To do so, PAA nanoparticles were replaced with the much smaller 8-arm PEG molecule "up to 10 nm" or "~10 nm". The 112 μL of chlorin e6 (Ce6) solution (20 mg/mL in DMF) was activated with 38.7 μL of N,N'-Dicyclohexylcarbodiimide (DCC, 20 mg/mL in DMF) and 43.2 μL of N-Hydroxysuccinimide (NHS, 20 mg/mL in DMF). After 30 min stirring, this solution was added into 50 mg of 8-arm-PEG solution (40 kDa, 20 mg/mL in DMF) and it was stirred overnight. To remove unreacted Ce6, the crude product was washed with enough 60% ethanol, PBS (pH 7.4) and D.I. water using Amicon filtration system (10 kDa filter membrane). The Ce6 conjugated 8-arm-PEG was obtained through freeze drying. Based on the UV-vis spectra of Ce6 conjugated 8-arm-PEG, it was confirmed that 1.4 of Ce6 was conjugated to one 8-arm-PEG (47%).

For CTP targeting, 620 µL of bi-functional conjugating PEG (MAL-PEG-NHS, 2 kDa, 100 mg/mL in PBS (pH 7.4)) was added into 2.22 mL of Ce6-8-arm PEG (20 mg/mL in PBS (pH 7.4)) and stirred 30 min. By amicon centrifugal cell (10 kDa), unreacted MAL-PEG-NHS was washed three times and dissolved in 2.5 mL of PBS (pH 7.4) and 240 µL of CTP (100 mg/mL in D.I. water). After overnight stirring, 1.9 mg of cysteine (10 mg/mL in D.I. water) was added and washed with enough D.I. water through amicon centrifugal cell (10 kDa). The final CTP-Ce6-8-arm PEG was obtained through freeze drying. In vivo testing was repeated with -CTP-Ce6-8-arm PEG. Adult male rats were sedated and a tail vein injection with -CTP-Ce6/Rh-8-arm PEG- at 1 mg/ml in PBS solution-was performed. After 1-7 hours hearts were removed and tissue samples were collected. After slide mounting, confocal microscopy was performed. As shown on the middle and right panels of FIG. 8, CTP-Ce6-8-arm PEG nanoplatform successfully crossed the vessel endothelium after about 3 hours.

Figure 9:
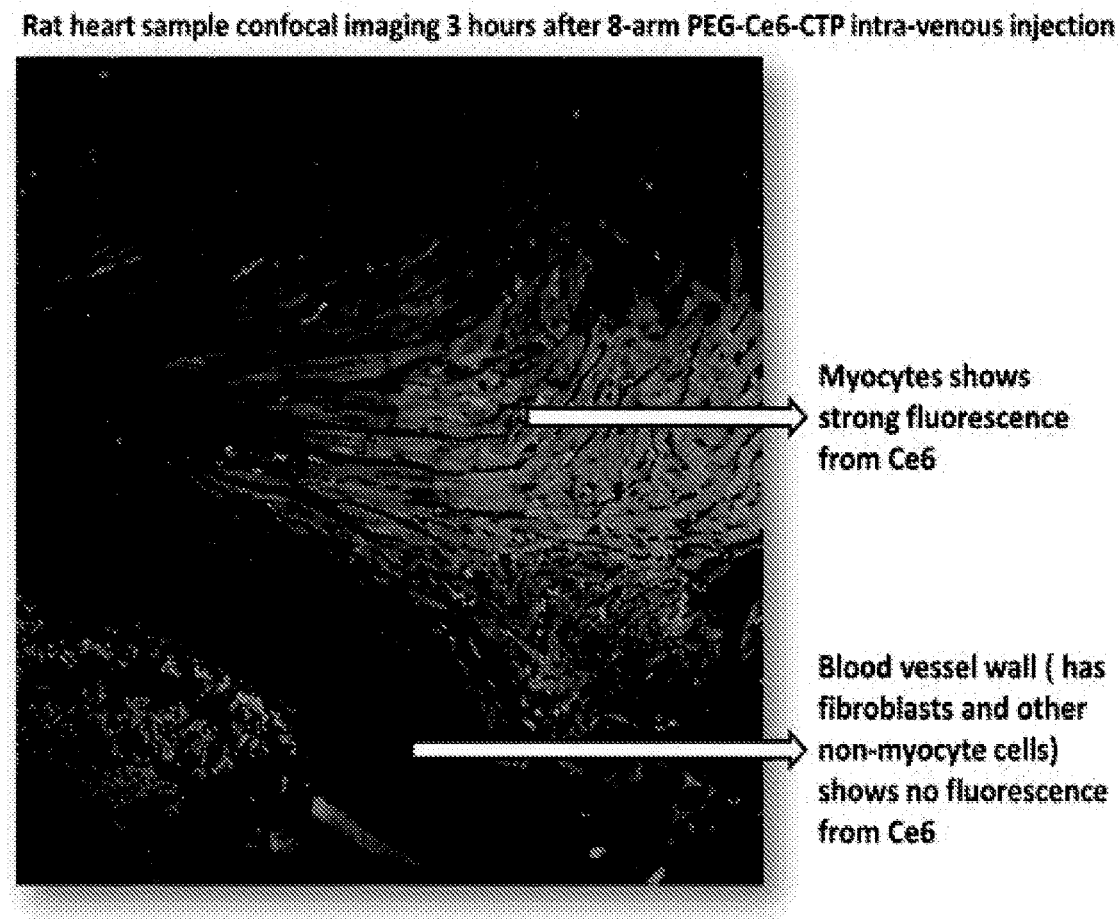
FIG. 9 shows targeting of particles to cardiac myocytes using Ce6 photosensitizer.

In vivo demonstration of nanoplatform blood stability and specific attachment to myocytes. Methylene blue was replaced with Ce6 M because methylene blue was decreased in vivo because of the action of blood reducing enzymes. On the other hand, Ce6 is known to remain stable when injected in blood. In vivo testing as described above was repeated with an improved CTP-Ce6-8-arm-PEG platform as described above. Results are shown in FIG. 9. Three hours after having injected CTP-Ce6-8-arm PEG into the rat tail vein, confocal imaging of tissue samples showed intense fluorescence in the myocytes indicating that 8-arm PEG-Ce6-CTP succeeded in crossing the endothelial lining and in attaching specifically to myocytes. In comparison, blood vessel wall non-myocyte cells such as fibroblasts did not show Ce6 fluorescence.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in molecular biology, genetics, or related fields are intended to be within the scope of the following claims.

What is claimed is:

1. A method of ablating cardiomyocytes, comprising:
   a) contacting an animal with a nanoparticle comprising a polymeric or glass matrix, a photosensitizer, and a cardiac targeting peptide, wherein said cardiac targeting peptide has the amino acid sequence of SEQ ID NO:1; wherein said cardiac targeting peptide is specific to cardiomyocytes; and
   b) administering light to activate said photosensitizer to at least a portion of the cardiomyocytes of said animal, wherein said administering results in ablation of the cardiomyocytes where said light is administered.

2. The method of claim 1, wherein said light is emitted from a laser.

3. The method of claim 1, wherein said photosensitizer is selected from the group consisting of methylene blue, chlorin e6 (Ce6), porfimer sodium, 2-devinyl-2-(1-hexyloxy-ethyl) pyropheophorbide (HPPH), coomasie blue and gold.

4. The method of claim 1, wherein said contacting is via intravenous administration.

5. The method of claim 1, wherein said animal is a human.

6. The method of claim 1, wherein said animal exhibits atrial fibrillation and said ablation reduces said atrial fibrillation relative to the level of atrial fibrillation prior to said ablation.

7. The method of claim 1, further comprising the step of imaging said nanoparticle in said animal.

8. The method of claim 7, further comprising the step of determining a treatment course of action based on said imaging, wherein said treatment course of action comprises repeating the step of administering said activator and/or nanoparticles when said imaging identifies cardiac tissue in need of ablating.

9. The method of claim 1, wherein said nanoparticle is approximately 10 nm or less in size.

10. The method of claim 1, wherein said polymeric or glass matrix is selected from the group consisting of polyacrylamide, polyvinylchloride, decy-methacrylate, and a sol-gel, and polyethylene glycol (PEG).

* * * * *

UNITED STATES PATENT AND TRADEMARK OFFICE
CERTIFICATE OF CORRECTION

| | | |
|---|---|---|
| PATENT NO. | : 10,512,691 B2 | Page 1 of 1 |
| APPLICATION NO. | : 14/396533 | |
| DATED | : December 24, 2019 | |
| INVENTOR(S) | : Jerome Kalifa et al. | |

It is certified that error appears in the above-identified patent and that said Letters Patent is hereby corrected as shown below:

On the Title Page

Item (71) reads:
"Applicants: THE REGENTS OF THE UNIVERSITY OF MICHIGAN, Ann Arbor, MI (US); Jerome Kalifa, Oak Park, MI (US); Raoul Kopelman, Ann Arbor, MI (US); Uma Mahesh R. Avula, Ypsilanti, MI (US); Gwangseong Kim, Ann Arbor, MI (US); Yong-Eun Koo Lee, Seoul (KR); Hyung Ki Yoon, Ann Arbor, MI (US)"

Whereas it should read:
"Applicants: THE REGENTS OF THE UNIVERSITY OF MICHIGAN, Ann Arbor, MI (US)"

Signed and Sealed this
Third Day of May, 2022

Katherine Kelly Vidal
*Director of the United States Patent and Trademark Office*